United States Patent [19]
Griffin et al.

[11] Patent Number: 6,015,827
[45] Date of Patent: Jan. 18, 2000

[54] BENZOXAZOLE-4-CARBOXAMIDES AND THEIR USE IN INHIBITING POLY (ADP-RIBOSE) POLYMERASE ACTIVITY AND IMPROVING CYTOTOXIC EFFECTIVENESS OF CYTOTOXIC DRUGS OR RADIOTHERAPY

[75] Inventors: Roger John Griffin, Northumberland; Alan Hilary Calvert; Nicola Jane Curtin, both of Tyne & Wear; David Richard Newell, Northumberland; Bernard Thomas Golding, Newcastle Upon Tyne, all of United Kingdom

[73] Assignee: Newcastle University Ventures Limited

[21] Appl. No.: 09/056,928

[22] Filed: Apr. 8, 1998

Related U.S. Application Data

[62] Division of application No. 08/706,326, Aug. 30, 1996, Pat. No. 5,756,510, which is a continuation of application No. PCT/GB95/00513, Mar. 9, 1995.

[30] Foreign Application Priority Data

Mar. 9, 1994 [GB] United Kingdom ............... 9404485

[51] Int. Cl.$^7$ ................... C07D 413/02; C07D 263/57; A61K 31/42
[52] U.S. Cl. .................... 514/394; 548/217; 548/224; 546/268.4
[58] Field of Search .................. 548/217, 224; 514/394; 546/268.4

[56] References Cited

U.S. PATENT DOCUMENTS

| Re. 26,565 | 4/1969 | Rodgers | 200/251 |
|---|---|---|---|
| 4,281,127 | 7/1981 | LeMahieu | 544/287 |
| 4,323,503 | 4/1982 | Thominet et al. | 260/340.3 |
| 4,499,303 | 2/1985 | Wyrick et al. | 514/605 |
| 5,032,617 | 7/1991 | Lee et al. | 514/617 |
| 5,079,248 | 1/1992 | Cross et al. | 514/237.5 |
| 5,223,539 | 6/1993 | Nosal et al. | 514/622 |
| 5,412,099 | 5/1995 | Goldmann et al. | 548/180 |
| 5,464,871 | 11/1995 | Kun et al. | 514/617 |
| 5,587,384 | 12/1996 | Zhang et al. | 514/309 |

FOREIGN PATENT DOCUMENTS

| 054 132 | 6/1982 | European Pat. Off. . |
|---|---|---|
| 305 008 | 3/1989 | European Pat. Off. . |
| 411 766 | 2/1991 | European Pat. Off. . |
| 512 870 | 11/1992 | European Pat. Off. . |
| 32 20 898 | 12/1983 | Germany . |
| 41 42 366 | 6/1993 | Germany . |
| 1338 235 | 11/1973 | United Kingdom . |
| 2 090 249 | 7/1982 | United Kingdom . |
| 91/18591 | 12/1991 | WIPO . |
| 93/07868 | 4/1993 | WIPO . |
| 93/12095 | 6/1993 | WIPO . |

OTHER PUBLICATIONS

Sinha et al., Quinazolones: Part XI–Effect of Substituents on Claisen Rearrangement of Allyloxyquinazolones, Indian Journal of Chemistry, Nov. 1985, pp. 1182–1184.
Joshi et al., Studies in Quinazolones: . . . , Indian Journal of Chemistry, Dec. 1978, pp. 1067–1072.
Yazima et al., Synthesis of Furoquinolines, Agric. Biol. Chem. 44(2), Feb. 1980, pp. 235–243.
Dean et al., N–Ethoxycarbonylamidines as Starting . . . , Journal of Heterocyclic Chemistry, vol. 19, No. 1, Jan.–Feb. 1982, pp. 171–176.
Armarego et al., Quinazolines, Part IX–Covalent Hydration . . . , J. Chem. Soc., 1967, pp. 449–454.
Mitscher et al., Quinolone Antimicrobial Agents . . . , J. of Medicinal Chemistry, vol. 22, No. 11, 1979, pp. 1354–1357.
Partridge et al., Cyclic Amidines. Part XV. Derivatives of Tricyccloquinazoline, J. of Chem. Soc., 1962, pp. 2549–2556.
L.V. Coates et al, Chem. Abstr., vol. 54, No. 13, 1960.
Chim. Ther. No. 4, 1967, pp. 231–239.
Coates et al, The Prpearation and Evaluation . . . , Jun. 1959, pp. 240–249.
Khi.Geteritski.Soedin., 70, 1970, pp. 855–858.
Dallacker et al, Uber Amino–benzo [1.3]dioxole, 1978, pp. 459–464., Z. Naturforsch, vol. 133c (7–8).
Spiteller, Der o–Effekt in den Massenspekktren aromatischer Verbindungen, Aug. 31, 1961, pp. 1147–1154., M.H. Chen., vol. 92, pp. 1147–1154.
Chemical Abstracts 54: 13054e., (1960).
Grotjahn et al, Cobalt–meditated [2+2+2] Cycloaddition of Alkynes to the Enamine Double Bond: A Formal Total Synthesis of Y–Lycorane, Synthesis, (6), pp. 579–605 (1993).
Taniguchi et al, Chem. Abstract 110:88635j, (1989).
Berger et al, Chem. Abstract 90:121395, (1979).

*Primary Examiner*—Mukund J. Shah
*Assistant Examiner*—Pavanaram K Sripada
*Attorney, Agent, or Firm*—Pillsbury Madison & Sutro, LLP

[57] ABSTRACT

Benzoxazole carboxamides are disclosed which can act as potent inhibitors of the DNA repair enzyme poly(ADP-ribose) polymerase or PARP enzyme (EC 2.4.2.30), and which thereby can provide useful therapeutic compounds for use in conjunction with DNA-damaging cytotoxic drugs or radiotherapy to potentiate the effects of the latter. Representative of the compounds are 2-methyl, 2-t-butyl, 2-phenyl or 2-(4-methoxyphenyl) benzoxazole-4-carboxamide.

9 Claims, No Drawings

BENZOXAZOLE-4-CARBOXAMIDES AND THEIR USE IN INHIBITING POLY (ADP-RIBOSE) POLYMERASE ACTIVITY AND IMPROVING CYTOTOXIC EFFECTIVENESS OF CYTOTOXIC DRUGS OR RADIOTHERAPY

This is a division of application Ser. No. 08/706,326, filed Aug. 30, 1996, now U.S. Pat. No. 5,756,510, which is a continuation of PCT/GB95/00513, filed Mar. 9, 1995, designating the U.S.

The present invention relates to benzamide analogues, especially certain 3-substituted benzamide compounds and related quinazolinone compounds that are of interest as being at least potentially useful chemotherapeutic agents by virtue of an ability to inhibit the activity of the enzyme poly ADP-ribosyltransferase (EC 2.4.2.30), also known as poly (ADP-ribose) polymerase, commonly referred to as ADPRT or PARP. In general, the latter abbreviation, PARP, will be used throughout the present specification.

BACKGROUND

At least in higher organisms, the enzyme poly ADP-ribosyltransferase is known to catalyse a transfer of the ADP-ribose moiety from the oxidized form $NAD^+$ of nicotinamide adenine dinucleotide to nuclear acceptor proteins so as to form homo ADP-ribose polymers, and this process has been implicated in a number of cellular events such as, for example, repair of DNA damage, development of cellular differentiation, transformation of cells by oncogenes, and gene expression. A common feature in a number of these processes is the formation and repair of DNA strand breaks and the stage which involves the PARP enzyme appears to be that of DNA ligase II-mediated strand rejoining. In the majority of cases a role for poly ADP-ribosylation has been implicated by the use of inhibitor of the PARP enzyme, and this has led to suggestions that such inhibitors, by interfering with the intracellular DNA repair mechanism, may have a useful chemotherapeutic role insofar as they should be able to modify treatmen resistance characteristics and potentiate or enhance the effectiveness of cytotoxic drugs in chemotherapy or of radiation in radiotherapy where a primary effect of the treatment is that of causing DNA damage in target cells, as for example in many forms of antitumour therapy.

In this connection, several classes of PARP inhibitors are already known, including benzamide itself and various nicotinamide and benzamide analogues, especially 3-substituted benzamides with small substituent groups such as 3-amino, 3-hydroxy and 3-methoxy. PARP inhibitory activity of certain N-substituted benzamides has also been reported in EP-A-0305008 wherein it has also been proposed to use these compounds in medicine for increasing the cytotoxicity of radiation or of chemotherapeutic drugs.

Regarding this use of benzamides as chemotherapeutic agents, a number of studies on such compounds that are known to exhibit PARP inhibitory activity have confirmed that they can potentiate the cytoxicity of a range of antitumour agents in vitro, for example, bleomycin and methylating drugs. More limited data has further indicated that such benzamides can also potentiate the activity of cytotoxic drugs in vivo, although the dose requirement have appeared to be rather high (e.g. in the region of 0.5 g kg$^{-1}$ per dose for 3-aminobenzamide) and there may be associated problems in preparing satisfactory pharmaceutical formulations and in avoiding toxicity limitations. Furthermore, a number of the known benzamides have also been shown clearly to have potential as radiosensitizers. increasing for example ionising radiation-induced tumour cell kill both in vitro and in vivo, and it is believd that in many cases this effect is related to these compounds acting as PARP inhibitors and interfering with DNA repair.

However, notwithstanding the existing data from in vitro and in viva studies suggesting that PARP inhibitors have considerable potential as useful chemotherapeutic agents which merit further clinical evaluation, for instance in connection with cancer therapy, currently available known PARP inhibitors are not considered as yet to be entirely suitable to represent candidate drugs. Accordingly, there is a need to find and develop a greater range of compounds having potentially useful PARP inhibitory properties.

DISCLOSURE OF THE INVENTION

The present invention identifies a new range or ranges of compounds of interest as PARP inhibitors that can be useful in medicine, especially when administered in conjunction with at least certain cytotoxic drugs or with radiotherapy for increasing the cytotoxic effectiveness thereof. In general, the compounds of this invention as hereinbelow defined comprise novel 3-substituted benzamide compounds, especially 3-oxybenzamide compounds, or analogues, of which many include relatively large or bulky 3-position substituents or include 3-position substituents linked in a ring structure with substituents in the 2-position. The compounds also include certain quinazolinones of which at least some may be formed by molecular rearrangement of related benzamide compounds. By virtue of their structure in general such compounds are adapted to act as an alternative substrate to $NAD^+$ for the PARP enzyme.

More specifically, from one aspect, the invention provides novel compounds selected from: (A), a 3-substituted benzamide compound having the general structural formula I

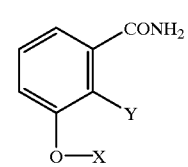

I or a pharmaceutically acceptable salt thereof, and (B), a quinazolinone compound having the general structural formula II

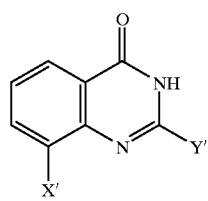

II or a pharmaceutically acceptable salt thereof, chracterised in that in structural formula I
   (i) Y is hydrogen, and
      X is —CH$_2$—Z
         wherein
         Z represents alkyl, an optionally substituted aralkyl group, —CH=CHR (where R is H, alkyl or an optionally substituted phenyl group), cyclohexyl, or a group having the structural formula III

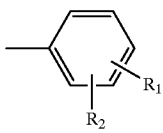

where $R_1$ is selected from H, alkoxy, $NO_2$, $N_3$, $NH_2$, $NHCOR_3$ ($R_3$ being alkyl or aryl), $CO_2R_4$ ($R_4$ being H or alkyl), alkyl, hydroxyalkyl, $CW_3$ or W (W being halide), and CN, and where $R_2$ is H, or where $R_1$ and $R_2$ together represent a group —O—$CHR_5$—O— bridging adjacent ring C's with $R_5$ being H, alkyl or an optionally substituted aralkyl or aryl group or (ii) Y is hydrogen, and X is —$(CH_2)_n$—Z wherein n is in the range of 5 to 12, and Z is halide or a purin-9-yl moiety; or (iii) Y and X together form a bridge —Y—X— that represents the grouping

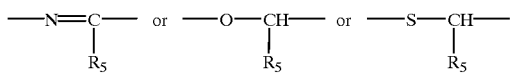

where $R_5$ is as specified above, and in structural formula II

X' represents hydroxyl, alkyl, alkoxy or an optionally substituted aryl (e.g. phenyl) or aralkyl (e.g. benzyl) group, and Y' represents hydrogen, alkyl or an optionally substituted aryl (e.g. phenyl) or aralkyl (e.g. benzyl) group.

Alkyl groups when present as such or as a moiety in other groups such as alkoxy, excluding in some cases the methylene chain —$(CH_2)_n$— specified above, will generally be composed of 1–8 carbon atoms, preferably 1–6 carbon atoms, and more usually 1–4 carbon atoms.

One very important group of compounds of special interest from the point of view of PARP-inhibitory activity comprises benzoxazole-4-carboxamide compounds, i.e. compounds represented by the formula IV

where $R_5$, if not H, is preferably alkyl, phenyl or another aryl group such as naphthyl or pyridyl. When $R_5$ is an alkyl group this will generally be $C_{1-6}$ alkyl, such as for example methyl, ethyl, n-propyl, i-propyl, n-butyl, t-butyl or cyclohexyl. However, it may in some cases be larger, such as in adamantyl for instance. When $R_5$ is a phenyl group this may be substituted, especially in the 4 (para) position but alternatively perhaps in the 2-position or 3-position, by substituents such as alkoxy for example. Within this group of benzoxazole compounds preferred members which are of particular interest include 2-methylbenzoxazole-4-carboxamide, 2-t-butylbenzoxazole-4-carboxamide, 2-phenylbenzoxazole-4-carboxamide, 2-(4-methoxyphenyl)benzoxazole-4-carboxamide.

In the above-mentioned compounds of formula IV, wherein there is an electron-rich aromatic ring, it is believed that the carboxamide group is constrained in a fixed conformation, particularly favourable for presenting the compound as an alternative substrate to $NAD^+$ for the PARP enzyme, by an intramolecular hydrogen bond between the ring nitrogen atom and one of the hydrogen atoms of the carboxamide group. A similar, although probably somewhat weaker effect may also occur in other compounds of formula I where the X and Y substituents form a bridge, as define under (iii) above, containing an oxygen or sulphur atom, i.e. where the ring N atom of the benzoxazoles of formula IV is replaced by an O or S atom.

It has, however, also been found that in attempting to prepare benzoxazole-4-carboxamide compounds of formula IV, in some methods of preparation which could be expected to yield the desired compound the product is liable to undergo a molecular rearrangement (especially if liquid ammonia is used to form the carboxamide) and an 8-hydroxy quinazolinone derivative is obtained instead of the expected benzoxazole. Unexpectedly, it has been found that at least some such quinazolinone derivatives, which may of course be prepared by various methods, possess a potentially very useful biological activity as PARP inhibitors of high activity. Accordingly, these quinazolinone compounds which generally conform to structural formula II represent another very important aspect of the present invention. Examples of such compounds which are of particular interest include:

(a) 8-hydroxy-2-methylquinazolin-4-[3H]one;

(b) 8-hydroxyquinazolin-4-[3H]one;

(c) 8-hydroxy-2-(4-nitrophenyl)-quinazolin-4-one;

(d) 8-methoxy-2-methylquinazolin-4[3H]-one;

(e) 8-methoxy-2-phenylquinazolin-4[3H]-one;

(f) 8-hydroxy-2-phenylquinazolin-4[3H]-one;

(g) 2,8-dimethylquinazolin-4[3H]-one.

Another important group of compounds of particular interest comprises 3-benzyloxybenzamides (BOB benzamide analogues) where X is a benzyl or substituted benzyl group. Examples of benzyl group substituents include 2-nitro (or another 2-substituent), 4-$CH_3$, 4-$CO_2H$, 4-$CO_2CH_3$, 4-$CONH_2$, 4-CN, 4-$CH_2OH$, 4-NHCOPh, and within this group specific compounds of particular interest include 3-benzyloxybenzamide, 3-(4-methoxybenzyloxy)benzamide, 3-(4-nitrobenzyloxy)benzamide, 3-(4-azidobenzyloxy)benzamide, 3-(4-bromobenzyloxy)benzamide, 3-(4-fluorobenzyloxy)benzamide, 3-(4-aminobenzyloxy)benzamide, 3-(3-nitrobenzyloxy)benzamide, 3-(3,4-methylenedioxyphenylmethyloxy)benzamide or 3-(piperonyloxy)benzamide, 3-(N-acetyl-4-aminobenzyloxy)benzamide, 3-(4-trifluoromethylbenzyloxy)beniamide, 3-(4-cyanobenzyloxy)benzamide,
3-(4-carboxymethylbenzyloxy)benzamide,
3-(2-nitrobenzyloxy)benzamide,
3-(4-carboxybenzyloxy)benzamide.

In some cases the aromatic ring of the benzyl moiety in compounds of the above group of BOB analogues may be hydrogenated and still show some PARP inhibitory activity, one example of a compound in this category being 3-cyclohexylmethyloxy)benzamide.

A further important group of compounds in accordance with the invention comprises the 3-oxybenzamides where there is a chain of 5 or more methylene groups terminating in a halogen atom, e.g. Br, or in a purin-9-yl moiety, especially adenine or 6-chloropurine. Specific compounds of interest within this group include 3-(5-bromopentyloxy)benzamide,
3-(8-adenos-9-yloctyloxy)benzamide,
3-[5-(6-chloropurin-9-yl)pentyloxy]benzamide,
3-(5-adenos-9-ylpentyloxy)benzamide,
3-[-(6-chloropurin-9-yl)octyloxy]benzamide,
3-[12-(6-chloropurin-9-yl)dodecyloxy]benzamide,
3-(12-adenos-9-yldodecyloxy)benzamide.

In addition, however, particularly interesting compounds are provided when the 3-position oxy-substituent includes a double bond such as in an allyl group, for example 3-allyloxybenzamide, or a cinnamyl group, for example 3-cinnamyloxybenzamide.

In another group of preferred compounds the 3-position oxy-substituent comprises an alkyl group having at least 4 carbon atoms. Typical examples include 3-butoxybenzamide,
3-pentyloxybenzamide,
3-hexyloxybenzamide,
3-heptyloxybenzamide,
3-octyloxybenzamide.

The invention also embraces or extends to methods of preparing compounds as hereinbefore defined (including intermediates in some cases) and to the therapeutic use of such compounds. This includes their use for making medical or veterinary preparations or pharmaceutical formulations containing an effective PARP inhibitory amount of the active compound for administration to a patient in conjunction with a cytotoxic drug or radiotherapy in order to increase the cytotoxic effectiveness of the latter. Such preparations or formulations may be made up in accordance with any of the methods well known in the art of pharmacy for administration in any suitable manner, for example orally, parenterally (including subcutaneously, intramuscularly or intravenously), or topically, the mode of administration, type of preparations or formulation and the dosage being generally determined by the details of the associated cytotoxic drug chemotherapy or radiotherapy that is to be enhanced.

As indicated, the compounds according to this invention have at least potential as PARP inhibitors, and in vitro tests hereinafter described have demonstrated positive pharmacological activity which it is believed reflects the activity to be found in vivo in the course of therapeutic clinical use.

It will be understood that where reference is made in this specification to compounds of formula I or II (or formula IV) such reference should be construed as extending also to their pharmaceutically acceptable salts where relevant. Also, where any of the compounds referred to can exist in more than one enantiomeric form, all such forms, mixtures thereof, and their preparation and uses are within the scope of the invention.

In general, many of the compounds of the present invention, including at least the benzyloxybenzamide (BOB) and allyl 3-oxybenzamide analogues, are conveniently prepared by a base-catalysed alkylation of 3-hydroxybenzamide, e.g. reaction in the presence of acetonitrile and potassium carbonate, using an appropriate alkylating agent (e.g. an alkyl halide R-Hal) which, if not available commercially, can be prepared via conventional methods. Initially, since 3-hydroxybenzamide itself is not widely available commercially, this compound can first be prepared by reacting commercially available 3-hydroxybenzoic acid with a mixture of triethylamine and ethyl chloroformate in dichloromethane to give a mixed anhydride that is quenched in liquid ammonia, or by a newly developed efficient, high yield, preparative route involving selective acetylation of the 3-position —OH of 3-hydroxybenzoic acid and subsequent conversion of the carboxyl group to carboxamide, as hereinafter described.

DESCRIPTION OF EXAMPLES OF PREFERRED EMBODIMENTS

The following examples and descriptions of stages in synthetic routes of preparation of various preferred compounds of interest serve to further illustrate the present invention, but should not be construed in any way as a limitation thereof.

In the first example (EXAMPLE 1), the above-mentioned new method of preparing 3-hydroxybenzamide from 3-hydroxybenzoic acid will be described since the 3-hydroxybenzamide is a starting material for the preparation of other benzamide analogues hereinafter described.

EXAMPLE 1

3-Hydroxybenzamide (a) 1st Stage—Preparation of 3-Acetoxybenzoic acid

3-Hydroxybenzoic acid (1 g; 7.29 mM) was added to a cooled solution of sodium hydroxide (0.61 g; 15.2 mM dissolved in 2 ml of water). Cooled acetic anhydride (0.81 g; 7.9 mM) was added with crushed ice (2 g). The mixture was stirred for 1 hour, and acidified with 6 M hydrochloric acid (3 ml) to yield a white precipitate. The organics were extracted into dichloromethane (3×30 ml), and dried over magnesium sulphate. The solvent was filtered and then removed under vacuum to yield a white solid which was recrystallised from boiling water.

Solvent for Thin-layer chromatography (T.L.C.): 10% methanol/90% dichloromethane; NMR: 200 MHz: $d_6$DMSO: $\delta$=2.4 (s;3H;$CH_3$); 7.45(m;1H;H$\delta$); 7.6 (t;1H;H$\beta$); 7.78(m;1H;H); 7.9(t;1H;H$\alpha$); 13.1(s;1H;O$\underline{H}$); Yield 86%

(b) 2nd Stage—Preparation of 3-Hydroxybenzamide

3-Acetoxybenzoic acid (0.5 g;) from the first stage was dissolved in thionyl chloride (1.74 ml) and refluxed for 3½ hours.

Excess thionyl chloride was removed by distillation to yield a yellow oil, which was added dropwise to a cooled solution of ammonia (35% aq) and stirred for 30 minutes. The mixture was boiled to a reduced volume (50%) and left to cool. 3-hydroxybenzamide crystallised out of solution and was collected and then recrystallised from boiling water.

T.L.C.: 10% methanol/90% dichloromethane; NMR: 200 MHz; $d_6$DMSO; $\delta$: 7.0 (1H; dt; $H_4$); 7.25(m; 4H; NH; $H_2$; $H_5$; $H_6$); 8.0(s; 1H; NH); 9.77(s; 1H; O$\underline{H}$). Yield 60%

EXAMPLE 2
3-(4-Azidobenzyloxy)benzamide (Compound NU1013)

(a) 1st Stage—Preparation of p-Azidotoluene p-Toluidine (9.3 mM) was dissolved in hydrochloric acid (5M; 10 ml), and the mixture cooled to <0° C. Sodium nitrite (10.28 mM) was dissolved in a minimum amount of water, and this solution was added dropwise to the reaction over 30 minutes. The solution was stirred for 20 minutes, then the presence of the oxidising agent was tested for using starch/iodide paper. Sodium azide (37.38 mM) was then added slowly to the reaction mixture over a period of 1 hour (due to vigorous effervescing). The reaction was quenched, once all the sodium azide had been added, in water (50 ml), and quantitatively transferred to a conical flask with water (50 ml). The mixture was neutralised with sodium carbonate, until pH=6. The organics were extracted into dichloromethane (3×30 ml), washed with water (2×20 ml), dried over magnesium sulphate, and excess solvent removed under vacuum. The p-azidotoluene thus obtained was an oil and was isolated via chromatography (100% petroleum/ether 40–60). $^1$H NMR: $d_6$ DMSO: δ: 2.37 (s; 3H; $CH_3$); 7.0 (d;2H; $H_3;H_5$); 7.3 (d; 2H; $H_2$; $H_6$)

(b) 2nd Stage—Bromination of p-Azidotoluene

To p-azidotoluene (2.2 mM) prepared as above was added N-bromosuccinimide (2.48 mM), and azo-isobutyronitrile (0.214 mM) in anhydrous benzene (5 ml). This was left to reflux for 5 hours, with the reaction being monitored by TLC. The organics were extracted into diethyl ether (3×15 ml), and water, dried over magnesium sulphate, and the excess solvent removed under vacuum. The p-azidobenzyl bromide formed was isolated using chromatographic techniques.

(c) Final Stage—Preparation of p-Azidobenzyl-3-Oxybenzamide

To 3-hydroxybenzamide (2.0 mM) under nitrogen was added anhydrous acetonitrile (20 ml), potassium carbonate (2.0 mM), and p-azidobenzyl bromide (2.0 mM). The mixture was refluxed for 3 hours, and the progress of the reaction monitored by TLC. The excess solvent was removed under vacuum, until dry, and the title compound was recrystallised from hot dichloromethane (minimum amount). A pale yellow crystalline solid was isolated and dried.

Melting point: 167–168° C. Infrared data: $cm^{-1}$: 3341;3155;2121;2094;1631;1583. Mass spectra: m\z: 269 ($M^{+1}$) 252;223;167;104 (100%); 93;77. $^1$H NMR: $d_6$-DMSO δ=5.5 (s; 2H; $CH_2$); 7.27 (m; 3H; $H_2'$; $H_6'$; $H_4$); 7.41–7.6 (m: 6H; $H_3'$; $H_5'$; $H_2$; $H_6$; $H_5$; NH); 8.0 (s; 1H; NH); $^{13}$C NMR: δ=69.098; 114.049; 118.164; 119.528; 120.359; 129.735; 129.886; 134.188; 136.096; 139.332; 158.480; 167.889; Elemental Analysis: Expect C: 62.68%; H: 4.47%; N: 20.89%; Found C: 62.18%; H: 4.30%; N: 20.70%.

EXAMPLE 3
3-(4-Bromobenzyloxy)benzamide (Comoound NU1014)

To 3-hydroxybenzamide (2.0 mM) under nitrogen was added anhydrous acetonitrile (20 ml), potassium carbonate (2.0 mM), and p-bromobenzyl bromide (2.0 mM). The mixture was refluxed for 3 hours, and the progress of the reaction monitored by TLC. The excess solvent was removed under vacuum, until dry, and the title compound was recrystallised from hot dichloromethane (minimum amount). A white crystalline solid was isolated and dried. Melting point: 160–161° C.; Infrared data: $cm^{-1}$: KBr disc: 3323; 3146; 1670; 1622. $^1$H NMR: $d_6$DMSO: δ=5.26 (s; 2H; $CH_2$); 7.3 (dd; 1H: $H_4$); 7.49–7.75 (m, 9H; PhBr; $NH_2$; PhO); $^{13}$C NMR: $d_6$DMSO: δ=114.031; 118.123; 120.402; 121.295; 129.704; 130.107; 131.690; 136.094; 136.723; 158.371; 167.843. Mass spectra: m/z: EI: 307 (M+1); 262; 212; 169 (100%) 101;90. Elemental analysis: Expect C: 55.26%; H: 3.29%; N: 4.61%; Found C: 54.61%; H: 3.66%; N: 4.47%.

EXAMPLE 4
3-(4-Fluorobenzyloxy)benzamide (Compound NU1015)

To 3-hydroxybenzamide (2.0 mM) under nitrogen was added anhydrous acetonitrile (30 ml), potassium carbonate (2.0 mM), and p-fluorobenzyl bromide (2.0 mM). The mixture was refluxed for 14 hours, and the progress of the reaction monitored by TLC. The excess solvent was removed under vacuum, until dry, and the title compound was recrystallised from hot dichloromethane (minimum amount), and petrol ether 40/60. A white crystalline solid was isolated and dried. Melting point: 161–162° C. Infrared data: KBr disc: $cm^{-1}$: 3366; 3171; $^1$H NMR: $d_6$DMSO: δ=5.23 (s; 2H; $CH_2$); 7.26–7.68 (m; 9H; NH; aromatics); 8.11 (s; 1H; $H_4$);

$^{13}$C NMR: $d_6$DMSO: δ=68.914; 113.951; 115.405; 115.821; 118.124; 120.329; 129,329; 130.255; 130.421; 133.487; 136.056; 158.464; 159.692; 164.546; 167.853.

Elemental analysis: Expect: C: 67.2; H: 4.8; N: 5.6; Found: C: 67.79; H: 4.81; N: 5.65.

EXAMPLE 5
3-(3-Nitrobenzyloxy)benzamide (Compound NU1017)

To 3-hydroxybenzamide (2.0 mM) under nitrogen was added anhydrous acetonitrile (20 ml), potassium carbonate (2.0 mM), and m-nitrobenzyl bromide (2.0 mM). The mixture was refluxed for 3 hours, and the progress of the reaction monitored by TLC. The excess solvent was removed under vacuum, until dry, and the title compound was recrystallised from hot dichloromethane (minimum amount). A white crystalline solid was isolated and dried.

Melting point: 162–163° C.

Infrared data: KBr disc: 3362; 3171; 1655; 1622. Mass spectrum: EI: m/z: 272(M+); 136(100%); 105;90;77.

$^1$H NMR: $d_6$DMSO: δ=5.42(s; 2H; $CH_2$): 7.28–7.33; (m;1H;Hα); 7.45–7.66 (m;4H;NH;$H_2$;$H_5$;$H_6$); 7.8 (t;1H;$H_5$'); 8.0(m:2H;NH;$H_6$'); 8.3 (m:1H;$H_4$'): 8.4 (m;1H;$H_2$') $^{13}$C NMR: $d_6$DMSO: δ=68.354; 114.041; 118.124; 120.589; 122.317; 123.120; 129.812; 130.435; 134.406; 136.132; 139.661; 148.185; 158.185; 167.774.

Elemental analysis: Expect: C: 61.76; H: 4.41; N: 10.11; Found : C: 61.53; H: 4.32; N: 10.01.

EXAMPLE 6
3-(N-acetyl-4-aminobenzyloxy)benzamide (Compound NU1030)

To Compound NU1013 (100 mg; 0.375 mM) from Example 2 was added thioacetic acid (2 ml) and this was left to stir at room temperature until the reaction was completed. The reaction was followed by T.L.C. 10% MeOH: 90% $CH_2Cl_2$. The product was then isolated via chromatography, and recrystallised from ethyl acetate and ether, to yield a white crystalline solid (30%).

Melting point: 198–199° C.

$^1$H NMR: δ: 2.19 (s;3H;$CH_3$); 5.2(s;2H;$CH_2$); 7.3 (m;1H;$H_4$); 7.4–7.8 (m; 8H; NH; $H_2$; $H_5$; $H_6$; $H_2'$; $H_3'$; $H_4'$; $H_6'$) 8.1 (s; 1H; NH); 10.1 (s; 1H; HNCO) $^{13}$C NMR: δ: 29.223, 74.412, 118.899, 123.013, 124.087, 125.108, 133.699, 134.557, 136.463, 140.921, 144.296, 163.685, 172.781.

EXAMPLE 7
3-(Piperonyloxy)benzamide (Compound NU1020)

1st Stage—Preparation of Piperonyl Chloride

Piperonyl alcohol (1 g; 6.57 mM) was dissolved in diethyl ether (10 ml), and to this was slowly added concentrated hydrochloric acid (3.81 ml). This was left to stir for 30 minutes. The excess solvent was removed to yield a colourless oil which crystallised at 4° C., (99%).

$^1$H NMR: d: 4.8 (s,2H,CH$_2$); 6.2(s,2H,OCH$_2$O); 7.0(m, 3H,aromatics).

2nd Stage—Preparation of Piperonyl BOB

To 3-hydroxybenzamide (137 mg; 1 mM) was added potassium carbonate (138 mg; 1 mM) and this was dissolved in anhydrous acetonitrile under a nitrogen atmosphere. To this was added piperonyl chloride (270 mg; 1 mM), and the mixture left to reflux for 15 hours. The organics were extracted into dichloromethane (3×20 ml), dried over magnesium sulphate, and the solvent removed under vacuum. The product was isolated using chromatographic techniques, with 20% petrol:80% ethyl acetate as eluant. A white solid was isolated which was recrystallised from hot water (97%). Melting point: 141–142° C.

$^1$H NMR: d$_6$DMSO: δ: 5.1 (s;2H;CH$_2$); 6.1(s,2H; OCH$_2$O); 7.1 (m; 3H; H$_2$'; H$_5$'; H$_6$'); 7.25 (dd; 1H; H$_4$); 7.5 (m; 4H; NH; N$_2$; H$_5$; H$_6$); 8.05 (s; 1H; NH); $^{13}$C NMR: d$_6$DMSO: δ: 69.02; 101.36; 108.40; 108.80; 114.01; 118.12; 120.20; 121.89; 129.65; 136.00; 147.20; 146.62; 158.53; 167.84. Mass spectrum: EI: 271 (M$^+$); 135 (100%); Elemental analysis: Expected C: 66.42; H: 4.79; N: 5.16; Found C: 66.18; H: 4.47; N: 4.94.

EXAMPLE 8
3-(4-Trifluoromethylbenzyloxy)benzamide (Compound NU1036)

3-hydroxybenzamide (0.137 g; 1 mmol) was dissolved in anhydrous acetonitrile (20 ml) under a nitrogen atmosphere. To this was added potassium carbonate (0.138 g; 1 mmol) and 4-(trifluoromethyl)benzyl bromide (0.155 ml; 1 mmol). This mixture was left to reflux for 17 hours.

The reaction was followed by TLC. Upon completion the acetonitrile was removed under reduced pressure to leave a white solid which was dissolved in water. The organics were extracted into dichloromethane (3×30 ml), dried over magnesium sulphate, filtered and the solvent removed under reduced pressure to leave a white crystalline solid which was recrystallised from boiling ethyl acetate and petrol (60–80).

M/Z (EI): 295 (35%; M$^+$) 159 (100%); $^1$H: 200 MHz: d$_6$ DMSO: δ: 5.4 (2H; S; CH$_3$); 7.3 (1H; m; H$_4$); 7.6 (4H; m; NH; H$_2$; H$_5$; H$_6$); 7.8 (2H; d; H$_2$'; H$_6$'); 7.9 (2H; d; H$_3$'; H$_5$'); 8.1 (1H; s; NH); $^{13}$C: 68.726; 114.011; 118.125; 120.513; 125.627; 125.693; 128.305; 129.007; 129.774; 136.133; 142.136; 158.296; 167.852; Elemental Analysis: Expected C: 61.02, H: 4.06, N: 4.75. Found C: 61.05/60.91, H: 3.94/3.96, N: 5.06/4.86.

EXAMPLE 9
3-(4-Cyanobenzyloxy)benzamide (Compound NU1037)

3-hydroxybenzamide (0.137 g; 1 mmol) was dissolved in anhydrous acetonitrile (20 ml) under a nitrogen atmosphere. To this was added potassium carbonate (0.138 g; 1 mmol) and 4-cyanobenzyl bromide (0.138 g; 1 mmol). This was left to reflux for 5 hours.

The reaction was followed by TLC. Upon completion the acetonitrile was removed under reduced pressure. Water was added to the remaining solid. The organics were extracted into dichloromethane (3×30 ml), dried over magnesium sulphate, filtered and the solvent removed under reduced pressure to leave a white crystalline solid which was recrystallised from boiling ethyl acetate and petrol (68%).

M/Z (EI) 252 (18% M$^+$); 153; 116 (75%); IR cm$^{-1}$ 3362, 3179 (amide NH$_2$); 2228 (C≡N); $^1$H: 200 MHz: d$_6$ DMSO: δ: 5.4 (2H; s; CH$_2$); 7.3 (1H; m; H$_4$); 7.65 (6H; m; H$_2$; H$_5$; H$_6$; NH; H$_2$'; H$_6$';); 8.0 (2H; d; H$_3$'; H$_5$'). $^{13}$C: 68.685; 110.848; 113.999; 118.153; 119.089; 120.555; 128.385; 1293792; 132.775; 136.133; 143.080; 158.222; 167.815. Elemental Analysis: Expected C: 71.43, H: 4.76, N: 11.11. Found: C: 71.27, H: 4.96, N: 10.67.

EXAMPLE 10
3-(4-carboxymethylbenzyloxy)benzamide (Compound NU1041)

To 3-hydroxybenzamide (1.37 g; 10 mmol) was added potassium carbonate (1.38 g; 10 mmol) and methyl 4-chloro-methylbenzoate (1.84 g; 10 mmol) in anhydrous acetonitrile (50 ml). The mixture was heated under reflux for 5 hours.

The acetonitrile was removed under reduced pressure, and the solids dissolved in water. The organics were extracted into dichloromethane (3×50 ml) and pooled. The solvent was dried over magnesium sulfate and removed under reduced pressure.

The solid was recrystallised from boiling ethyl acetate and petrol, collected and dried (65%).

IR: cm$^{-1}$, 3331; 3154, 2959. M/Z; 285 (48%; M$^+$), 254 (38%); 149 (100%) 121 (75%). $^1$H: d$_6$ DMSO: δ=3.9; (3H; s; CH$_3$), 5.25 (2H; OCH$_2$Ph), 7.25 (1H; d, H$_4$), 7.4 (5H; m; NH$_2$; H$_2$; H$_5$; H$_6$), 7.6 (2H; d; H$_2$'; H$_6$'), 709 (2H; d; H$_3$'; H$_5$'). $^{13}$C: 52.418; 68.948. 114.016; 118.093; 120.459; 127.792; 129.299; 129.669; 136.097; 142.786; 158.33; 166.312; 167.822. Elemental Analysis: Expected C 67.37%; H 5.26% N 4.91%. Found: C 67.19%; H 5.16%; N 4.78%

EXAMPLE 11
3-(2-Nitrobenzyloxy)benzamide (Compound NU1042)

To 3-hydroxybenzamide (0.137 g; 1 mmol) was added potassium carbonate (0.138 g; 1 mmol) and 2-nitrobenzyl bromide (0.216 g; 1 mmol) in anhydrous acetonitrile (10 ml). The mixture was heated under reflux for 5 hours.

The acetonitrile was removed under reduced pressure, and the solids dissolved in water. The organics were extracted into dichloromethane (3×20 ml) and pooled. The solvent was dried over magnesium sulfate and removed under reduced pressure.

The solid was recrystallised from boiling ethyl acetate and petrol, collected and dried.

IR cm$^{-1}$: 3368; 3196, M/Z; 272 (3.8%; M$^+$); 248; 217; 196; 181; 136 (100%). $^1$H: d$_6$ DMSO; δ=5.5 (2H; OCH$_2$Ph), 7.14 (1H; d, H$_4$), 7.4 (4H; m; NH; H$_2$'; H$_5$'; H$_6$), 7.26 (2H; m; H$_5$'; H$_4$'), 8.0 (1H; br; NH); 8.02 (1H; d; H$_3$'). $^{13}$C: 66.783; 113.854; 118.172; 120.753; 125.183; 129.490; 129.549; 132.679; 132.339; 136.136.; 147.786; 158.112; 167.778. Elemental Analysis: Required C 61.76%; H 4.41% N 10.29%; Found C 61.49%; H 4.42%; N 10.11%.

EXAMPLE 12
3-(4-carboxybenzyloxy)benzamide (Compound NU1052)

To 3-(4-carboxymethylbenzyloxy)benzamide (Compound NU1041) (0.03 g; 0.1 mmol) was added methanol (3 ml) and aqueous sodium hydroxide (1M; 3 ml). This was warmed to 40° C., and the reaction monitored. Upon the disappearance of the starting material the solution was acidified (aqueous HCl dropwise), and extracted into ethyl acetate (3×30 ml). The organics were pooled, dried over magnesium sulphate, and the solvent removed under reduced pressure. This yielded a white crystalline solid.

EXAMPLE 13
3-(Phenethyl)oxybenzamide (Compound NU1048)

3-Hydroxybenzamide (500 mg; 3.6 mM) was dissolved in dry acetonitrile (36 ml), and to this was added potassium carbonate (0.503 g; 3.6mmol) and 2-(bromoethyl)benzene (0.498 ml; 3.6 mmol). The mixture was heated under reflux for two days. The acetonitrile was removed under reduced pressure to yield a white solid. This was dissolved in water and extracted into dichloromethane (3×30 ml). The organics were pooled, dried over magnesium sulphate, filtered and the solvent was removed under reduced pressure to yield a white solid. This was recrystallised from boiling ethyl acetate and petrol (0.459 g; 12.51%). MPt: 132–136° C. $^1$H: 200 MHz CDCl$_3$ 3.05 (2H, t, H$_8$); 4.2 (2H, t, H$_7$); 6.00 (1H, br s, NH); 7.04 (1H, m, H$_4$); 7.27 (9H, m, NH; aromatic). IR cm$^{-1}$ 3300 (NH$_2$); 1666 (CO); 2930 (C=C). M/Z (EI); 241 (M$^+$; 18%); 105 (—COHN$_2$; 100%). Elemental Analysis: Expected % C$_{15}$H$_{15}$O$_2$N C: 74.4, H: 6.20, N: 5.79; Found: % C: 74.7, H:6.2, N:5.8.

EXAMPLE 14
3-Allyloxybenzamide (Compound NU1031)

To 3-hydroxybenzamide (274 mg; 2.0 mM) under a nitrogen atmosphere was added potassium carbonate (276 mg; 21.0 mM). This was dissolved in acetonitrile (20 ml) containing allyl bromide (169 ul; 2.0 mM). The mixture was refluxed for 5 hours, and the reaction followed by T.L.C.: 10% MeOH: 90% CH$_2$Cl$_2$. The excess solvent was then removed under vacuum, the organics extracted into dichloromethane, dried, and the solvent removed, to yield a white solid. This was recrystallised from hot water to produce a white "needle" solid (63%) as the final product. Melting point: 116–117° C. $^1$H NMR: δ=4.7(m;2H:He,Hf); 5.5(m;2H;Hh,Hi); 6.2(m;1H;Hg); 7.2(m;1H;Hd); 7.6m;4H;Ha,Hb,Hc,NH); 8.1(s;1H;NH). $^{13}$C NMR: δ=68.580, 113.821, 117.978, 129.661, 133.893, 136.025, 158.371, 167.892. Mass spectra: EI: 177 (M$^+$); 41 (100%)

EXAMPLE 15
3-(Cinnamyloxy)benzamide (Compound NU1050)

3-hydroxybenzamide (0.5 g 3.6 mmol) was dissolved in dry acetonitrile (50 ml). To this was added potassium carbonate (0.503 g; 3.6 mmol) and cinnamyl chloride (0.5 ml; 3.6 mmol). This was left to reflux for 3.5 hours. The acetonitrile was removed under reduced pressure yielding a white sold which was dissolved in water (80 ml). The organics were extracted in dichloromethane (3×30 ml), dried over magnesium sulphate, filtered and the solvent removed under reduced pressure leaving a white solid. The solid was recrystallised from ethyl acetate and petrol (45%).

MPt: 131–138° C. M/Z 137 (36%); 165 (100%, cinnamyl$^+$), 94 (48%); 77 (24%). IR cm$^{-1}$ 3400 & 3200 (NH$_2$), 1600 (C=O). $^1$H: 200 MHz d$_6$DMSO 4.88 (2H, d, H$_7$); 6.65 (1H, m, H$_8$); 6.94 (1H, m, H$_4$); 7.24 (1H, m, H$_4$); 7.5 (9H, m, aromatic & NH); 8.1 (1H, s, NH). Elemental Analysis: Expected C: 75.9%; H: 5.9%; N: 5.5%; Found C: 76.07%; H: 5.85*; N: 5.56%.

EXAMPLE 16
2-Methylbenzoxazole-4-carboxamide (Compound NU1056)

1st Stage—Preparing Methyl (3-Hydroxy-2-nitro) benzoate 3-hydroxy-2-nitrobenzoic acid (5 g; 27.32 mM) was dissolved in anhydrous methanol (200 ml). Anhydrous hydrogen chloride gas was bubbled through the solution until saturated. The mixture was then refluxed for 20 hours (reaction followed by T.L.C.: 10% methanol/90% dichloromethane). Next, the solvent was removed under vacuum to yield a brown solid. The solid was dissolved in water (100 ml) and sodium bicarbonate was added until effervescence stopped. Sodium chloride (15 g) was added to the aqueous solution, and the product was extracted into ethyl acetate (3×50 ml). The pooled aliquots were dried over magnesium sulphate and the solvent removed under vacuum to yield a malty brown solid.

T.L.C. (as before): r.f.: 0.53 NMR: 200 MHz: d$_6$ DMSO: δ=3.9 (s;3H;OCH$_3$); 7.1(m;1H;H$_4$); 7.35(m;1H;H$_6$); 7.8 (t;1H;H$_5$) Yield 92%

2nd Stage—Preparation of Methyl (2-Amino-3-hydroxy)-benzoate

Under a nitrogen atmosphere a palladium/carbon catalyst was suspended in anhydrous methanol (150 ml). To this suspension was added methyl (3-hydroxy-2-nitro) benzoate from Stage 1 (4 g; 20.3 mM). The mixture was left under a hydrogen atmosphere for 4½ hours. The catalyst was removed by filtration through a "celite" pad, and the solvent removed from the filtrate to yield an orange/brown product. T.L.C.: 40% Ethyl acetate/60% petroleum ether 60/80. r.f. 0.33; NMR 200mHz: d$_6$DMSO: δ: 3.81(S;3H;OCH$_3$); 6.2 (broad;2H;NH$_2$); 6.5(t;1H;H$_5$); 6.9(m;1HH$_6$) 7.3(m;1H;H$_4$) 9.8(s;1H;OH); Yield 83%.

3rd Stage—Preparation of Methyl 2-methylbenzoxazole-4-carboxylate

To a solution of the methyl (2-amino-3-hydroxy)-benzoate (3 g; 18.01 mM) in m-xylene (150 ml) was added acetyl chloride (1.518 ml; 21.6 mM). A precipitate was formed; this was left to stir for 30 minutes. On the addition of triethylamine (2.97 ml; 21.6 mM) the solution became translucent. Pyridinium-p-toluene sulphonic acid (1.2 g; 21.6 mM) was added, and the mixture refluxed for 34 hours. The solvent was removed by distillation (vacuum) to yield a brown solid which was column chromatographed (50% ethyl acetate/50% petrol 60/80) to give the desired product as a yellow solid. T.L.C. As above. $^1$HNMR :200 MHz; CDCl$_3$; δ: 2.69(3H;s;2—CH$_3$); 3.99(3H;s;OMe); 7.33 (3H;t;H$_6$); 7.63(1H;dd;H$_7$); 7.94(1H;dd;H$_5$).

4th Stage—Preparation of 2-methylbenzoxazole-4-carboxylic acid

Methyl 2-methylbenzoxazole-4-carboxylate (0.1 g, 0.523 mmol) was dissolved in methanol (3 ml), and to this was added aqueous sodium hydroxide solution (0.2 M, 3 ml). The mixture was stirred at 40° C. for 4 hours and acidified with hydrochloric acid (6 M) until pH=1.0. The mixture was extracted with ethyl acetate (3×20 ml), the combined organic layers were washed with water (2×20 ml), dried (MgSO$_4$) and the solvent was removed under reduced pressure to afford the carboxylic acid (0.068 g, 73%).

5th Stage—Preparation of 2-methylbenzoxazole-4-carboxamide

A solution of 2-methylbenzoxazole-4-arboxylic acid (0.1 g, 0.28 mmol) in anhydrous THF (10 ml) was stirred under nitrogen, and thionyl chloride (0.022 ml, 0.31 mmol), and DMF (0.1 m) were added, whereupon the mixture was stirred for a further 5 hours at room temperature. Aqueous ammonia (0.5 ml) was added and the mixture was stirred for a further 30 minutes. The solvent was removed under reduced pressure, the residual solid was dissolved in water (20 ml), and the solution was extracted with ethyl acetate (3×20 ml). The organic layers were pooled, washed with water (2×20 ml) and dried (MgSO$_4$). The solvent was removed under reduced pressure to furnish the carboxamide (0.083 g, 84%).

$^1$H (200 MHz) CDCl$_3$ δ=6.0 (brs, 1H, NH), 7.4 (t, 1H, H$_6$), 7.6 (dd, 1H, H$_7$), 8.15 (dd, 1H, H$_5$), 8.8 (brs, 1H, NH).

EXAMPLE 16a
2-Methylbenzoxazole-4-carboxamide (Compound NU1056)

In a modification of the procedure described under Example 16 above, the product of the 3rd stage, methyl 2-methylbenzoxazole-4-carboxylate, was prepared directly from the product of the 1st stage, as described below.

Methyl 3-hydroxy-2-nitrobenzoate (0.1 g; 0.59 mmol) from the 1st stage was dissolved in anhydrous ethanol (20 ml) and to this was added ethyl acetimidate hydrochloride (0.067 g; 0.59 mmol). The reaction mixture was then heated under reflux for 24 hours. The ethanol was removed under reduced pressure yielding a brown crystalline solid. This was dissolved in ethyl acetate (3×20 ml) to produce a precipitate of excess ethyl acetimidate hydrochloride. The excess imidate was filtered off and the solution washed with sodium hydroxide solution (0.1N; 3×20 ml), and water (3×50 ml). The solvent was dried over magnesium sulphate and removed under reduced pressure, leaving a orange crystalline solid (0.1265 g; 85%).

EXAMPLE 17
2-t-butylbenzoxazole-4-carboxamide (Compound NU1040)

(a) 1st Stage—Preparation of Methyl 2-t-butylbenzoxazole-4-carboxylate

2-Amino-3-hydroxybenzoate (0.1 g; 0.598 mmol) was dissolved in m-xylene and warmed to 70° C. To this was added pivaloyl chloride (0.117 ml; 0.958 mmol), whereupon a brown precipitate was observed to develop. The mixture was stirred for 30 minutes before the addition of triethylamine (0.099 ml; 0.958 mmol) and pyridinium-4-toluenesulphonate (0.04 g; 0.958mmol). The mixture was then heated under reflux for 26 hours. The m-xylene was removed under reduced pressure to yield a sticky brown solid. The solid was dissolved in water (50 ml) and the organics extracted into ethyl acetate (3×30 ml), pooled, dried over magnesium sulphate, filtered and the solvent removed under reduced pressure.

The title compound was purified via silica column chromatography, with 1:1 ethyl acetate:petrol as the eluant to yield a yellow solid (69%).

IR cm$^{-1}$: 3040 (3×CH$_3$), 1709 (C=O). M/Z; 233 (63%; M$^+$); 218 (50%; —CH$_3$) 202 (42%; —OCH$_3$); 186 (100%); 173 (12%; —CH$_3$); 160 (33%); 146 (62%); 117 (43%). $^1$H: d$_6$ DMSO: δ=1.17 (9H; s; (CCH$_3$)$_3$); 3.99 (3H; s, OCH$_3$); 7.31 (1H; t; H$_6$ J=8 Hz), 7.66 (lH; dd: H$_7$; J=7.8, 1 Hz), 7.95 (1H; dd; H$_5$ J=7, 1 Hz).

(b) 2nd Stage—Preparation of 2-t-Butylbenzoxazole-4-carboxamide

Methyl 2-t-butyl-4-benzoxazole carboxylate (0.1 g; 0.46mmol) was dissolved in methanol (5 ml), and to this was added aqueous ammonia (5 ml). The mixture was warmed to 40° C. and left to stir for 6 hours at ambient temperature. Once the reaction was complete the solvent was removed under reduced pressure and the product was recrystallised from boiling ethyl acetate and petrol (73%).

IR cm$^{-1}$: 3395; 3304 (amide NH); 3163 (3×CH$_3$), M/Z; 218 (96%; M$^+$); 202 (43%; —NH$_2$) 186 (85%; —CONH$_2$); 175 (77%); 160 (35%) 146 (79%); 133 (23%); 41 (100%). $^1$H: CDCl$_3$: δ=1.44 (9H; s; (CCH$_3$)$_3$); 5.95 (1H; br s; NH); 7.34 (1H; t; H$_6$ J=8 Hz), 7.6 (1H; dd: H$_7$; J=7, & 2 Hz) 8.07 (1H; dd; H$_5$ J=6.7, 2 Hz); 8.88 (1H; br s; NH) $^{13}$C 28.416 (3×CH$_3$), 34.372 (CCH$_3$), 113.905 (Ar), 123.277 (Ar), 124.338 (Ar), 124.338 (Ar), 125.440 (Ar), 139.371 (O-Ar), 150.804 (N-Ar), 166.457 (Ar), 174.471 (C=O amide). CHN: Found: C 65.915%; H 6.39%; N 12.48%, Required: C 66.038%; H 6.465%; N 12.835%.

EXAMPLE 18
2-Phenylbenzoxazole-4-carboxamide (Compound NU1051)

(a) 1st Stage—Preparation of Ethyl benzimidate Hydrochloride

Benzonitrile (0.514 ml; 5 mmol) was added to anhydrous ethanol (0.69 g). Anhydrous hydrogen chloride gas was bubbled through the solution until saturated. The mixture was left to stir for 20 hours. The white crystalline solid was collected and dried.

mpt: 125–130° C. IR: cm$^{-1}$, 2856, 1631. M/Z; 148 (M$^+$, 30%), 105 (100%); $^1$H: d$_6$ DMSO; δ=1.5 (3H; t, J=7 Hz; CH$_2$CH$_3$), 4.75 (2H; q, J=6.9 Hz; CH$_2$CH$_3$), 8.0 (5H; m; aromatics). Elemental Analysis: Expected C: 58.25; H: 6.51; N: 7.54; Found C: 58.13; H: 6.43; N: 7.36.

(b) 2nd Stage—Preparation of Methyl 2-phenylbenzoxazole-4-carboxylate

To Methyl 2-amino-3-hydroxybenzoate (0.10 g; 0.59 mmol) was added ethyl benzimidate hydrochloride (0.167 g; 0.998 mmol) in anhydrous ethanol (20 ml). This was refluxed for 20 hours, and the reaction followed by TLC (1:4 Ethyl acetate:petrol).

The ethanol was removed under reduced pressure and the solid dissolved in water (20 ml), the organics were extracted into ethyl acetate (3×20 ml), pooled, and washed with sodium hydroxide solution (2×10 ml; 0.2 M), water (2×10 ml) and then dried over magnesium sulfate. The solvent was removed under reduced pressure to yield a yellow solid. The title compound was isolated by flash chromatography (eluant as for TLC), yielding an off-white crystalline solid. (85%).

IR: cm$^{-1}$, 1714. $^1$H: d$_6$ DMSO: δ=4.1 (3H; s; OCH$_3$), 7.39 (1H; t; J=6 Hz; H$_6$), 7.5 (3H; m; H$_3$'; H$_4$'; H$_5$'), 7.78 (1H; dd J=7.0, 1.0 Hz; H$_7$;), 8.0 (1H; dd; J=6.67 & 1.14 Hz; H$_5$'), 8.3 (2H; m; H$_2$'; H$_6$').

(c) 3rd Stage—Preparation of 2-phenylbenzoxazole-4-carboxamide

To a solution of methyl 2-phenylbenzoxazole-4-carboxylate (0.02 g; 0.0905 mmol) in methanol (3 ml) was added aqueous ammonia (3 ml). This was warmed to 40° C. and left to stir, whilst the reaction was monitored by TLC (1:4 EtOAc:petrol). Once all the starting material had reacted a white precipitate was formed. The solvent was removed to yield a white solid, which was recrystallised from ethyl acetate and petrol (70%).

MPt: 199–201° C. $^1$H: CDCl$_3$: δ=6.02 (1H; br s: NH); 7.43 (1H; t; H$_6$; J=8 Hz), 7.57 (3H; m: H$_3$'; H$_4$'; H$_5$'), 7.74 (1H; dd; H$_7$; J=1 Hz, & 7 Hz); 8.23 (1H; dd; H$_5$; J=1 Hz & 7.3 Hz); 8.27 (2H; m; H$_2$'; H$_6$'), 8.97 (1H; br s; NH). $^{13}$C ; M/Z; (EI); 238 (m$^+$; 100%); 222 (—NH$_2$68%); 195 (—CONH$_2$; 98%). IR cm$^{-1}$ 3383; 3165. Elemental Analysis: Expected C:70.58, H:4.23, N:11.76. Found C:70.41, H:4.24, N:11.77.

EXAMPLE 19
2-(4-Nitrophenyl)benzoxazole-4-carboxamide (Compound NU1053)

(a) 1st Stage—Preparation of Methyl 3-hydroxy-2-(N-4-nitrobenzoyl)aminobenzoate

Methyl 2-amino-3-hydroxybenzoate (0.5 g; 2.099 mmol) was dissolved in m-xylene (40 ml) with warming to 60° C. 4-Nitrobenzoyl chloride (0.556 ml; 2.99 mmol) was added dropwise, and this was left to stir for 4 hours. The solution was cooled to ambient temperature and the m-xylene removed under reduced pressure. The solid was dissolved in water (100 ml) and the organics extracted into ethyl acetate (3×50 ml). The organic fractions were pooled, dried over magnesium sulphate, filtered and the solvent removed under reduced pressure. The title product was purified via column chromatography (1:4 ethyl acetate:petrol as eluent) to yield an orange solid.(49%).

IR: cm$^{-1}$: 3443 (OH), 2953, 1697, 1649, 1404. M/Z; 316 (15% M$^+$). $^1$H: CDCl$_3$: δ=3.95 (3H; s; OCH$_3$), 7.25 (1H; t; H$_5$ J=8 Hz), 7.31 (1H; dd; H$_4$,; J=6, & 2 Hz), 7.67 (1H; dd; H$_6$,); 8.26 (2H; dd; H$_2$'; H$_6$' J=2.3 Hz); 8.30 (2H; dd; H$_3$'; H$_5$' J=2.2 Hz); 9.81 (1H; s; OH); 12.30 (1H; s; NH).

(b) 2nd Stage—Preparation of Methyl 2-(4-nitrophenyl) benzoxazole-4-carboxylate

Methyl 3-hydroxy-2-(N-4-nitrobenzoyl)aminobenzoate (0.1 g; 0.34 mmol) was dissolved in m-xylene (20 ml), and to this was added triethylamine (0.033 ml; 0.45 mmol) and pyridinium-4-toluene sulphonate (0.070 g; 0.28 mmol). This was refluxed for 32 hours. The m-xylene was removed under reduced pressure and the remaining solid dissolved in water. The organics were extracted into ethyl acetate (3×30 ml), dried, filtered and the solvent removed under reduced pressure to yield a brick red solid (74%).

IR: cm$^{-1}$:, 1726; 1522; 1556, M/Z; 298 (84%, M$^+$) 267 (100%, —OCH$_3$), 240 (—CO) $^1$H: CDCl$_3$: δ=4.01 (3H; s; OCH$_3$), 7.44 (1H; t; H$_6$ J=8.1 Hz), 7.76 (1H; dd; H$_7$,; J=7.2, & 1 Hz), 8.04 (1H; dd; H$_5$,), 8.35 (2H; dd; H$_2$'; H$_6$' J=2.2 Hz); 8.46 (2H; d; H$_3$'; H$_5$' J=2.2 Hz).

(c) 3rd Stage—Preparation of 2-(4-nitrophenyl) benzoxazole-4-carboxylic acid

Methyl 2-(4-nitrophenyl)benzoxazole-4-carboxylate (0.1 g, 0.335 mmol) was dissolved in methanol (3 ml), and to this was added aqueous sodium hydroxide solution (0.2 M, 3 ml). The mixture was stirred at 40° C. for 4 hours and acidified with hydrochloric acid (6 M) until pH=1.0. The mixture was extracted with ethyl acetate (3×20 ml), the combined organic layers were washed with water (2×20 ml), dried (MgSO$_4$) and the solvent was removed under reduced pressure to afford the carboxylic acid (0.084 g, 89%).

(d) 4th Stage—Preparation of 2-(4-nitrophenyl) benzoxazole-4-carboxamide

A solution of 2-(4-nitrophenyl)benzoxazole-4-carboxylic acid (0.084 g, 0.29 mmol) in anhydrous THF (10 ml) was stirred under nitrogen, and thionyl chloride (0.022 ml, 0.31 mmol), and DMF (0.1 ml) were added, whereupon the mixture was stirred for a further 5 hours at room temperature. Aqueous ammonia (0.5 ml) was added and the mixture was stirred for a further 30 minutes. The solvent was removed under reduced pressure, the residual solid dissolved in water (20 ml), and the solution was extracted with ethyl acetate (3×20 ml). The organic layers were pooled, washed with water (2×20 ml) and dried (MgSO$_4$). The solvent was removed under reduced pressure to furnish the carboxamide (0.07 g, 85%.).

EXAMPLE 20

2-(4-Methoxyphenyl)benzoxazole-4-carboxamide (Compound NU1054)

(a) 1st Stage—Preparation of Methyl 3-hydroxy-2-(N-4-methoxybenzoyl)aminobenzoate Methyl 2-amino-3-hydroxybenzoate (0.5 g; 2.99 mmol) was dissolved in m-xylene (40 ml) with warming to 60° C. 4-Methoxybenzoyl chloride (0.509 g; 2.99 mmol) was added dropwise, and this was left to stir for 3 hours. The solution was cooled to ambient temperature and the m-xylene removed under reduced pressure. The solid was dissolved in water (100 ml) and the organics extracted into ethyl acetate (3×50 ml). The organic fractions were pooled, dried over magnesium sulphate, filtered and the solvent removed under reduced pressure. The title product was purified via chromatography (1:4 ethyl acetate:petrol as eluent) and recrystallised from boiling ethyl acetate/petrol to yield a brick red solid (33%). IR: cm$^{-1}$: 3100 (OH) 2571, 1691, 1643, 1606, M/Z; 301 (23%, M$^+$), 270 (—OCH$_3$), 135 (100%, COPhOCH$_3$) $^1$H: CDCl$_3$: δ=3.87 (3H; s; OCH$_3$); 3.93 (3H; s; COOCH$_3$), 7.02 (2H; dd; H$_5$'; H$_3$'); 7.14 (1H; t; H$_5$ J=8 Hz), 7.29 (1H; dd; H$_4$,; J=6.3, & 1.7 Hz), 7.63 (1H; dd; H$_6$); 8.03 (2H; dd; H$_2$'; H$_6$'); 10.38 (1H; s; OH); 11.98 (1H; s; NH).

(b) 2nd Stage—Preparation of Methyl 2-(4-methoxyphenyl) benzoxazole-4-carboxylate Methyl 3-hydroxy-2-(N-4-methoxybenzoyl) aminobenzoate (0.05 g; 0.166 mmol) was dissolved in m-xylene (20 ml), and to this was added triethylamine (0.016 ml; 0.215 mmol) and pyridinium-4-toluene sulphonate (0.034 g; 0.13 mmol). This was refluxed for 58 hours. The m-xylene was removed under reduced pressure and the remaining solid dissolved in water. The organics were extracted into ethyl acetate (3×30 ml), dried, filtered and the solvent removed under reduced pressure to yield a solid (74%).

IR cm$^{-1}$: 1718, 1614, 1502. M/Z; 283 (45%, M$^+$) 252 (31%, —OCH$_3$), 225, 63 (100%). $^1$H: CDCl$_3$: δ=3.88 (3H; s; COOCH$_3$); 6.9 (2H; d; H$_3$'; H$_5$'); 7.35 (1H; t; H$_6$), 7.74 (1H; dd; H$_7$;), 7.96 (1H; dd; H$_5$); 8.2 (2H; d; H$_2$'; H$_6$').

(c) 3rd Stage—Preparation of 2-(4-methoxyphenyl) benzoxazole-4-carboxamide

Methyl 2-(4-methoxyphenyl)benzoxazole-4-carboxylate was dissolved in liquid ammonia (30 ml) and sealed in an autoclave. The reaction mixture was left at 55° C., 20 bar for >20 hours. Once the reaction was complete the ammonia was removed and the resulting solid recrystallised from boiling ethyl acetate and petrol.

EXAMPLE 21

3-(5-Bromopentyloxy)benzamide (Compound NU1019)

A mixture of 3-hydroxybenzamide (0.5 g, 3.65 mmol), 1,5-dibromopentane (1.82 g, 1.1 ml, 7.3 mmol) and potassium carbonate (500 mg, 3.65 mmol) was refluxed (2 h) in acetonitrile (18 ml) until the reaction was complete by TLC. The solvent was then removed by rotary evaporation to leave a white sticky solid which was chromatographed (10% methanol in dichloromethane on silica) to give a white solid. This was recrystallised from a mixture of petrol and ethyl acetate to give white flaky crystals (0.744 g, 2.6 mmol, 70% yield). mp 98–99° C.

δ$_H$(200 MHz, d$_6$-DMSO): 8.09 (1H,s,NH), 7.49 (4H,m, H2,5, 6 and NH), 7.1 (1H,d,J 7.99, H4), 4.11 (2H,t,J 6.2,CH$_2$0), 3.67 (2H,t,J 6.6,2H), 1.90 (4H,m,CH$_2$CH$_2$CH$_2$), 1.62 (2H,m,CH$_2$); δ$_C$(200 MHz, d$_6$-DMSO): 168(CO), 158.85(C3), 129.63(C2), 120(C4), 117.79(C6), 113.53(C5), 67.73(OCH$_2$), 35.36(CH$_2$Br), 32.30(CH$_2$CH$_2$0), 28.12 (CH$_2$CH$_2$Br), 24.63 (OCH$_2$CH$_2$CH$_2$); M/Z (EI) 285(M$^+$). Elemental Analysis: Found: C: 50.71%, H: 5.36%, N: 4.95%. C$_{15}$H$_{22}$NO$_2$Br Requires C: 50.366%, H: 5.636%, N: 4,895%.

EXAMPLE 22

3-(8-N9-Adenine-octyloxy)benzamide (Compound NU1022)

A bomb reaction vessel was charged with a mixture (110 mg, 0.27 mmols) of 3-[8-N7-(6-chloropurine)octyloxy]-benzamide, 3-(8-N9-(6-chloropurine)octyloxy)benzamide and liquid ammonia and heated under pressure (64° C., 30 bar, 16H). The ammonia was evaporated to leave a yellow solid which was chromatographed (silica, 15% methanol/dichloromethane) to give a pale yellow solid which was recrystallised from methanol (56 mg, 0.17 mmol, 62% yield) mp 199–199.5° C. v cm$^{-1}$; δ$_H$ (200 MHz, d$_6$-DMSO) 8.24 (1H,s,purine H8), 8.23 (1H,s,purine H2), 8.06 (1H,s, CONH). 7.55–7.39 (4H,m,CONH and aromatic H2,5,6), 7.30 (2H,s,NH$_2$), 7.17–7.13 (1H,m,aromatic H4), 4.23 (2H, t,J 7, OCH$_2$), 4.07 (2H,t,J 6.3, CH$_2$N), 1.94–1.76 (4H,m, OCH$_2$CH$_2$ and CH$_2$CH$_2$N), 1.40 (8H,m,alkyl env); δ$_C$(200 MHz, d$_6$-DMSO) 167.998 (CO), 158.847 (C3), 152.711 (pC8), 141.206 (pC2), 136.047 (C1), 129.667 (CS), 119.967 (C6), 117.866 (C4), 113.592 (C2), 67.900 (OCH$_2$), 43.221 (NCH$_2$), 29,698 (OCH$_2$CH$_2$), 28.961 (OCH$_2$CH$_2$CH$_2$ and NCH$_2$CH$_2$), 26.313(OCH$_2$CH$_2$CH$_2$CH$_2$), 25.762 (NCH$_2$CH$_2$CH$_2$CH$_2$); m/z 338(M$^+$). Elemental Analysis: Found: C,62.42, H,6.48, N,21.89 C$_{20}$H$_{26}$N$_6$O$_2$; Requires: C,62.81, H,6.85, N,21.97%.

EXAMPLE 23
3-[5-(6-Chloropurin-9-yl)pentyloxy]benzamide (Compound NU1023)

A solution of 3-(bromopentyloxy)benzamide (500 mg, 1.7 mmols), 6-chloropurine (270 mg, 1.7 mmols) and potassium carbonate (240 mg, 1.7 mmols) in DMF (7.5 ml) was stirred for two days at room temperature. The solvent was then removed under vacuum (0.001 mmHg) and the white solid (mixture of N7 and N9 isomers) was chromatographed (silica, 10% MeOH/CH$_2$Cl$_2$) to give a single product (N9 isomer) as a glass. This was triturated with ether (~5 ml) to give a white solid which was recrystallised from ethyl acetate to give the product (120 mg, 0.33 mmols, 20% yield) mp 132–133° C. ν cm$^{-1}$; δ$_H$ (200 MHz, d$_6$-DMSO) 8.88(1H,s,purine H8), 8.85(1H,s,purine H2) 8.05(1H,s, CONH). 7.56(4H,m,NH and aromatic H2,5,6), 7.15–7.10 (1H,m,H4), 4.44(2H,t,J7, OCH$_2$), 4.08(2H,t,J6.3, CH$_2$N), 2.12–1.98(2H,m,OCH$_2$CH$_2$), 1.94–1.80(2H,m,NCH$_2$CH$_2$), 1.59–1.43(2H,m,CH$_2$CH$_2$CH$_2$); δ$_C$ (200 MHz, d$_6$-DMSO) 167.925(CO), 158.774(C3), 152.306(pC4), 151.760(pC8), 149.293(pC2), 136.019(CO), 131.175(pC6), 129.596(C5), 119.961(C6), 117.801(C4), 113.458(C2), 67.591(OCH$_2$), 44.033(NCH$_2$), 29.071(OCH$_2$CH$_2$), 28.337(CH$_2$CH$_2$N), 22.890(CH$_2$CH$_2$CH$_2$); m/z 360 (M$^+$). Elemental Analysis: Found C, 56.73, H, 5.28, N, 19.4. C$_{17}$H$_{18}$N$_5$O$_2$Cl; Requires C: 56.57%, H: 5.04%, H: 19.46%.

EXAMPLE 24
3-(5-Adenos-9-ylpentyloxy)benzamide (Compound NU1024)

A bomb reaction vessel was charged with a mixture (392.1 mg, 1.1 mmols) of 3-[5-N7-(6-chloropurine) pentyloxy]-benzamide, 3-[5-N9-(6-chloropurine)pentyloxy] benzamide and liquid ammonia and heated under pressure (66° C., 30 bar, 16H). The ammonia was evaporated away to leave a yellow solid that was chromatographed (silica, methanol/dichloromethane) to give a pale yellow solid which was recrystallised (203.5 mg, 0.6 mmols, 54% yield).

mp 148–149° C. ν cm$^{-1}$; δ$_H$ (200 MHz, d$_6$-DMSO) 8.25(2H,m,purine H8,2), 8.06(1H,s,CONH), 7.61–7.38(4H, m,CONH and aromatic H2,5,6), 7.31(2H,s,NH$_2$), 7.15–7.11 (1H,m,H4), 4.27(2H,t,J=7 Hz, OCH$_2$), 4.07(2H,t,J=6.3 Hz, CH$_2$N), 2.05–1.78(4H,m,OCH$_2$(CH$_2$)$_3$CH$_2$H), 1.56–1.41 (2H,m,NCH$_2$CH$_2$), 1.59–1.43(2H,m,CH$_2$CH$_2$CH$_2$); δ$_C$ m/z (M+).

EXAMPLE 25
3-[8-N9-(6-Chloropurine)-octyloxy]benzamide (Compound NU1027)

A solution of 3-(bromooctyloxy)benzamide (500 mg, 1.5 mmols), 6-chloropurine (236 mg, 1.5 mmols) and potassium carbonate (210 mg, 1.5 mmols) in DMF (7.5 ml) was stirred for two days at room temperature. The solvent was then removed under vacuum (0.001 mmHg) and the white solid remaining (composed of N7 and N9 isomers) was chromatographed (silica, 5% petrol/THF) to give a single product (N9 isomer) in the form of a white solid (74 mg) which was recrystallised (2×) from ethanol to give 58.7 mg (10% yield),

EXAMPLE 26
8-Hydroxy-2-(4-nitrophenyl)quinazolin-4-one (Compound NU1057)

Methyl 2-(4-nitrophenyl)benzoxazole-4-carboxylate (0.20 g) obtained as described in Example 19 (2nd stage) was dissolved in liquid ammonia (30 ml) and sealed in an autoclave. The reaction mixture was left at 55° C., 20 bar for 20 hours. Under these conditions, the expected 2-(4-nitrophenyl)benzoxazole derivative apparently rearranged to give the corresponding quinazolinone derivative. Once the reaction was complete the ammonia was removed and the resulting solid recrystallised from boiling ethyl acetate and petrol (84%).

IR cm$^{-1}$:, M/Z; 283 (38%, M$^+$) 267 (100%, —NH$_2$), 240 (—CO) $^1$H: CDCl$_3$: δ=7.35 (1H; dd; H$_5$), 7.5 (1H; t; H$_6$;), 7.7 (1H; dd; H$_7$); 8.45 (2H; d; H$_2$'; H$_6$'); 8.79 (2H; d; H$_3$'; H$_5$'), 9.98 (1H; br s; NH), 12.8 (1H; br s; NH).

Similarly, in attempting to prepare benzoxazole-4-carboxamide, the product underwent a molecular rearrangement yielding 8-hydroxy-quinazolin-4-[3H]one (Compound NU1026) which had quite strong PARP inhibitory activity.

Further examples now follow of the preparation of more quinazolinone compounds of particular interest.

EXAMPLE 27
8-Methoxy-2-methylquinazolin-4-[3H]-one (Compound NU1063)

Method A (a) 1st Stage—Preparation of 3-Methoxy-2-nitrobenzamide

A solution of 3-methoxy-2-nitrobenzoic acid (0.1 g, 5.1 mmol), thionyl chloride (0.55 ml, 7.6 mmol) and dimethylformamide (0.2 ml), in THF (10 ml) was stirred for 12 hours at 25° C. under nitrogen. Aqueous ammonia (6 ml) was cautiously added and the mixture was stirred for a further 15 minutes, the solvent was removed under reduced pressure and the remaining solid was washed with ice-cold water and collected (0.74 g, 75%) m.p. 219–222° C. δ$_H$ (200 MHz, d$_6$-DMSO) 4.01 (s, 3H, OCH$_3$); 7.41–7.46 (dd, 1H, Ar-4H); 7.55–7.60 (dd, 1H, Ar-6H); 7.69 7.77 (m, 1H, Ar-5H); 7.84 (br s, 1H, —NH); 8.31 (br s, 1H, —NH); m/z 196 (34.3%, M$^+$) ν$_{max}$/cm$^{-1}$ 3350 (br), 3180 (br), 3000, 2970, 2920, 2820, 1675. Elemental analysis: found C 49.03, H 3.93, N 13.97, C$_8$H$_8$N$_2$O$_4$ requires C 48.98, H 4.11, N 14.28%. H(b) 2nd Stage—Preparation of 2-Amino-3-methoxybenzamide 3-Methoxy-2-nitrobenzamide (0.5 g, 2.5 mmol) was dissolved in dry methanol (40 ml) and hydrogenated using palladium-carbon catalyst (80 mg). The catalyst was removed by filtration through Celite, and the residual product (0.35 g) was collected and dried (83%) m.p. 145–147° C. δ$_H$(200 MHz, d$_6$-DMSO) 3.88 (s, 3H, —OCH$_3$); 6.40 (br s, 2H, —NH$_2$); 6.54–6.62 (t, 1H, Ar-5H); 6.96–6.99 (dd, 1H, Ar-4H); 7.23 (br s, 1H, —NH); 7.29–7.33 (dd, 1H, Ar-6H); 7.85 (br s, 1H, —NH); m/z 166 (43.8%, M$^+$) ν$_{max}$/cm$^{-1}$ 3480, 3370, 3330, 3150, 2970, 2850, 1680, 1620. Elemental analysis: found C 57.54, H 5.99, N 16.61, C$_8$H$_{10}$N$_2$O$_2$ requires C 57.82, H 6.07, N 16.86%.

(c) 3rd Stage—Preparation of 2-N-Acetylamino-3-methoxybenzamide

To a solution of 2-amino-3-methoxybenzamide (0.5 g, 3 mmol) in dry THF (15 ml), containing pyridine (0.3 ml; 3.9 mmol), was added acetyl chloride (0.2 ml, 3.3. mmol) in THF (2 ml) dropwise, and the reaction mixture was stirred overnight under nitrogen. The solvent was removed under vacuum and the remaining white slurry washed with aqueous sodium bicarbonate solution, filtered and washed with water. The white product (0.19 g, 31 %) was collected and dried.

m.p. 243–246° C.

$\delta_H$ (200 MHz, d$_6$-DMSO) 2.05 (s, 3H, —C$\underline{H}_3$); 3.88 (s, 3H, —OC$\underline{H}_3$); 7.14–7.18 (dd, 1H, Ar-4$\underline{H}$); 7.21–7.25 (dd, 1H, Ar-6$\underline{H}$); 7.33–7.41 (m, 2H, —NH and Ar-5$\underline{H}$; 7.53 (br s, 1H, —N$\underline{H}$); 9.27 (br s, 1H,—N$\underline{H}$); m/z 208 (16.6, M$^+$) $\nu_{max}$/cm$^{-1}$ 3420, 3240 (br), 3160, 3020, 2980, 2870, 1660. Elemental analysis: found C 56.98, H 5.38, N 12.78, C$_{10}$H$_{12}$N$_2$O$_3$ requires C 57.68, H 5.81, N 13.46%.

(d) Final Stage—Preparation of 8-Methoxy-2-methylauinazolin-4-[3H]-one

2-N-Acetylamino-3-methoxybenzamide (0.07 g, 0.34 mmol) from 3rd stage was dissolved in aqueous sodium hydroxide solution (2% w/v, 2 ml) and the solution was stirred for 12 hours at 25° C. The reaction mixture was neutralised with dilute aqueous hydrochloric acid and the resulting white precipitate that was deposited was collected by filtration and washed thoroughly with water. The title compound was recrystallised from ethyl acetate (0.043 g, 67%) m.p. 202–204° C. (sublimes).

EXAMPLE 28
8-Methoxy-2-methylquinazolin-4-[3H]-one (Compound NU1063)
Alternative Method B To a mixture of 2-amino-3-methoxybenzamide (1.0 g, 6 mmol) from the 2nd stage of Example 28 and pyridine (0.6 ml, 7.8 mmol) in dry THF (25 ml), was added a solution of acetyl chloride (0.9 ml, 13 mmol) in THF (2 ml) dropwise, and the mixture was stirred overnight under nitrogen. The solvent was removed under vacuum and the remaining white slurry was resuspended in 2% aqueous sodium hydroxide solution and neutralised with aqueous hydrochloric acid, whereupon a white precipitate formed. The product was collected by filtration and recrystallised from methanol-water (0.915 g, 80%) m.p. 202–204° C. (sublimes) $\delta_H$ (200 MHz, d$_6$-DMSO) 2.43 (s, 3H, —C$\underline{H}_3$); 3.97 (s, 3H, —OC$\underline{H}_3$); 7.37–7.50 (m, 2H, Ar-6/7$\underline{H}$); 7.68–7.73 (dd, 1H, Ar-5 $\underline{H}$); $\delta_C$ (d$_6$-DMSO); 21.83 (—$\underline{C}$H$_3$); 56.05 (—O$\underline{C}$H$_3$); 114.96, 116.99 (Ar-67$\underline{C}$); 121.95 ($\underline{C}$—CH$_3$); 126.5 (Ar-5$\underline{C}$); 140.0 (Ar-8A$\underline{C}$); 153.26 (Ar-8$\underline{C}$); 154.33 (Ar-4a$\underline{C}$); 162.04 ($\underline{C}$=O); m/z 190 (96.6%, M$^+$) $\nu_{max}$/cm$^{-1}$ 3171, 3034, 2903, 1676, 1620, 1574, 1483. Elemental analysis: found C 62.14, 62.36, H 5.18, 5.29, N 14.23, 14.36; C$_{10}$H$_{10}$N$_2$O$_2$ requires C 63.15, H 5.30, N 14.73%.

EXAMPLE 29
8-Hydroxy-2-methylquinazolin-4-[3H]-one (Compound NU1025)

A solution of 8-methoxy-2-methylquinazolin-4-[3H]-one (0.7 g, 3.7 mmol) from Example 28 in BBr$_3$ (1.0 M in CH$_2$Cl$_2$) 8.4 ml, 8.4 mmol) was heated under reflux for 24 hours under nitrogen. Solvents were removed by distillation under vacuum and the remaining residue was hydrolysed with sodium hydroxide solution (10% w/v). Acidification with aqueous hydrochloric acid afforded a white precipitate, which was removed. The filtrate was extracted with ethyl acetate (3×30 ml), dried (MgSO$_4$) and the solvent was removed under vacuum. Recrystallisation from propan-2-ol-water afforded the target compound (65%) m.p. 253–258° C.

$\delta_H$ (200 MHz, d$_6$-DMSO) 2.48 (s, 3H, —C$\underline{H}_3$); 7.22–7.41 (m, 2H, Ar=6/7$\underline{H}$); 7.57–7.62 (dd, 1H, Ar-5$\underline{H}$); 9.57 (s, 1H, —O$\underline{H}$); 12.26 (s, 1H, —N$\underline{H}$); $\delta_C$ (d$_6$-DMSO); 21.72 (—$\underline{C}$H$_3$); 115.78, 118.42 (Ar-6/7$\underline{C}$); 121.76 ($\underline{C}$—CH$_3$); 126.54 (Ar-5$\underline{C}$); 138.27 (Ar-8a$\underline{C}$) 152.58 (Ar-8$\underline{C}$); 152.87 (Ar-4a$\underline{C}$); 162.05 ($\underline{C}$=O); m/z 176 (100%, M$^+$); $\nu_{max}$/cm$^{-1}$ 3320, 3175, 3030, 2900, 2800, 1670. Elemental analysis: found C 61.39, H 4.54, N 15.88, C$_9$H$_8$N$_2$O$_2$ requires C 61.36, H 4.58, N15.94%.

EXAMPLE 30
8-Methoxy-2-phenylquinazolin-4-[3H]-one (Comnound NU1065)
Method A (a) 1st Stage—Preparation of 2-N-Benzoylamino-3-methoxybenzamide To a stirred solution of 2-amino-3-methoxybenzamide (0.5 g, 3 mmol) from the 2nd stage of Example 28 in dry THF (15 ml), containing pyridine (0.3 ml, 3.0 mmol), was added benzoyl chloride (0.4 ml, 3.3 mmol) in THF (2 ml) dropwise. The reaction mixture was stirred under nitrogen at 25° C. The solvent was removed under vacuum to afford a white slurry which was washed with sodium bicarbonate solution, filtered and washed with water. Recrystallisation from methancl-water afforded the title compound (0.2 g, 41%) m.p. 176–180° C.; $\delta_H$ (200MH, d$_6$-DMSO) 3.88 (s, 3H, —OC$\underline{H}_3$); 7.24–7.32 (m, 2H, Ar-4/6$\underline{H}$); 7.41–7.49 (m, 2H, —N$\underline{H}$, Ar-5$\underline{H}$); 7.59–7.73 (m, 4H, —N$\underline{H}$, Ph-3'/4'$\underline{H}$); 8.04–8.08 (dd, 2H, Ph-2'$\underline{H}$); 9.85 (s, 1H, —N$\underline{H}$); mlz 270 (74.6%, M$^+$).

(b) 2nd Stage—Preparation of 8-Methoxy-2-phenyl quinazolin-4-[3H]-one

2-N-Benzoylamino-3-methoxybenzamide (0.2 g, 0.74 mmol) was dissolved in aqueous sodium hydroxide solution (2% w/v, 2 ml) and the solution was stirred at room temperature for 12 hours. The reaction mixture was neutralised with hydrochloric acid, and the resulting white precipitate that formed was collected by filtration and recrystallised from methanol/water (0.12 g, 65%) m.p. 252–256° C.

EXAMPLE 30
8-Methoxy-2-phenylquinazolin-4-[3H]-one (Compound NU1065)
Alternative Method B To a solution of 2-amino-3-methoxybenzamide (1.0 g, 6 mmol) (from the 2nd stage of Example 28) and pyridine (0.6 ml, 7.8 mmol) in dry THF (25 ml), was added a solution of benzoyl chloride (O.8 ml, 6.6 mmol) in THF (2 ml) dropwise, and the mixture was stirred overnight under nitrogen. The solvent was removed under vacuum and the remaining white slurry was resuspended in 2% aqueous sodium hydroxide solution and neutralised with aqueous hydrochloric acid, whereupon a white precipitate formed. The product was collected by filtration and recrystallised from methanol-water (1.1 g, 75%) m.p. 252–256° C.; $\delta_H$ (200 MHz, d$_6$-DMSO) 4.06 (s, 3H, —OC$\underline{H}_3$); 7.47–7.61 (m, 2H, Ar-4/6$\underline{H}$); 7.63–7.69 (m, 3H, Ph-3'/4'$\underline{H}$); 7.80–7.85 (dd, 1H, Ar-5$\underline{H}$); 8.27–8.32 (m, 2H, Ph-2'$\underline{H}$); 12.70 (s, 1H, —N $\underline{H}$); m/z 252 (100%, M$^+$); $\nu_{max}$/cm$^{-1}$ 3330, 3190, 3170, 3120, 3070, 2950, 2890, 2830, 1660.

Elemental analysis: found C 71.38, H 4.39, N 11.17, C$_{15}$H$_{12}$N$_2$O$_2$ requires C 71.42, H 4.79, N 11.10%.

EXAMPLE 31
8-Hydroxy-2-phenylquinazolin-4-[3H]-one (Compound NU1068)

A solution of 8-methoxy-2-phenylquinazolin-4-[3H]-one (0.5 g, 2 mmol) from Example 30 or 30a in BBr$_3$ (1.0 M in CH$_2$Cl$_2$) (6 ml, 6 mmol) was heated under reflux for 24 hours under nitrogen. Solvents were removed by distillation under vacuum and the remaining residue was hydrolysed with sodium hydroxide solution (10% w/v). Acidification with aqueous hydrochloric acid afforded a white precipitate, which was removed. The filtrate was extracted with ethyl acetate (3×30 ml), dried (MgSO$_4$) and the solvent was removed under vacuum. Recrystallisation from propan-2-ol afforded the target compound (0.187 mg, 67%) m.p. 280–284° C.; $\delta_H$ (200 MHz), d$_6$-DMSO) 7.73–7.50 (m, 2H, Ar-6/7H̲); 7.66–7.72 (m, 4H, Ar-5H̲, Ph-3'/4'H̲); 8.51–8.54 (dd, 2H, Ph-2H̲); 9.75 (bs, 1H, —OH̲); 12.60 (bs,. 1H, —NH̲); $\delta_C$ (d$_6$-DMSO); 116.01, 118.68 (Ar=6/7C̲); 122.03 ( C̲-Ph); 127.43–128.76 (Ph-1'/2'/3'/4'C̲); 137.98 (Ar 8aC̲); 150.72 (Ar-8C̲); 153.31 (Ar-4aC̲); 162.62 (C═O); m/z 238 (100%, M$^+$); $\nu_{max}$/cm$^{-1}$ (approx. values) 3380 (br), 3180, 3120, 3050, 2940, 1640.

Elemental analysis: found C 69.54, H 4.05, N 11.46, C$_{14}$H$_{10}$N$_2$O$_2$ requires C 70.58, H 4.23, N 1176%.

EXAMPLE 32

2,8-Dimethylquinazolin-4-[3H]-one (Compound NU1069)

To a solution of 2-amino-3-methylbenzamide (0.5 g, 3.3 mmol) (prepared by conventional methods) and pyridine (0.35 ml, 4.3 mmol) in dry THF (15 ml), was added a solution of acetyl chloride (0.36 ml, 5.0 mmol) in THF (2 ml) dropwise, and the mixture was stirred overnight under nitrogen. The solvent was removed under vacuum and the remaining white slurry was resuspended in 2% aqueous sodium hydroxide solution and neutralised with aqueous hydrochloric acid, whereupon a white precipitate formed. The solid was collected and recrystallised from methanol-water to furnish the required quinazolinone (0.47 g, 81%) m.p. 217–220° C.;

$\delta_H$ (200 MHz, d$_6$-DMSO) 2.44 (s, 3H, —CH̲$_3$); 2.57 (s, 3H, —CH̲$_3$); 7.36–7.44 (t, 1H, Ar-6H̲); 7.68–7.72 (dd, 1H, Ar-7H̲); 7.97–8.01 (dd, 1H, Ar-5H̲); 12.25 (br s, 1H, —NH̲); m/z 174 (100%, M$^+$); $\nu_{max}$/cm$^{-1}$ 3325, 3180, 3040, 2990, 2910, 2880, 2795, 1680, 1620.

Elemental analysis: found C 68.76, H 5.57, N 15.90, C$_{10}$H$_{10}$N$_2$O requires C 68.94, H 5.76, N 16.08%.

ASSAY FOR PARP INHIBITORY ACTIVITY

Compounds of the present invention, particularly those detailed in the preceding Examples, have been tested in vitro for activity as PARP inhibitors using the following methods and materials.

In principle, the PARP assay used relies upon activating endogenous PARP (as hereinafter described) in cells containing exogenous [$^{32}$P]-NAD$^+$ introduced therein by suspending the cells in a solution of [$^{32}$P]-NAD$^+$ to which they have been rendered permeable in an initial pre-treatment step. The poly(ADP-ribose) which is then synthesised by the enzyme can be precipitated by trichloracetic acid (TCA) and the amount of radio-labelled $^{32}$P incorporated therein measured, e.g. using a scintillation counter, to give a measure of the activity of the PARP under the particular conditions of the experiment. By repeating the experiment following the same procedure, and under the same conditions, in the presence of each compound to be tested the reduction in enzyme activity, representative of the inhibitory effect of the test compound, can then be ascertained from the reduction, if any, of the amount of [$^{32}$P] measured in the TCA precipitated poly(ADP-ribose).

The results of this assay may be expressed in terms of percentage inhibition or reduction in activity for one or more different concentrations of each compound tested, or it may be expressed in terms of that concentration of the tested compound which reduces the enzyme activity by 50%, i.e. the IC$_{50}$ value. Thus, with a range of different compounds a set of comparative values for inhibitory activity can be obtained.

In practice, L1210 murine leukaemia cells were used as the source of the PARP enzyme after being rendered permeable to exogenous [$^{32}$P]NAD by exposure to hypotonic buffer and cold shock. In the preferred technique developed, which has been found to give exact and reproducible results, a defined amount of a small synthetic oligonucleotide, in particular a single strand oligonucleotide having the palindromic sequence CGGAATTCCG, is introduced into the cell suspension for activating the PARP enzyme. This oligonucleotide sequence snaps back on itself to form a double-stranded molecule with a single blunt end and provides an effective substrate for activation of PARP. Its behaviour as a potent activator of the enzyme was confirmed in the tests carried out.

The experimental protocol adopted, in which a synthetic oligonucleotide as mentioned above is introduced as a specific activator of PARP, discriminates between PARP and other mono-ADP-ribosyltransferases in the cells. Thus, introduction of such synthetic oligonucleotides causes a 5 to 6 fold stimulation in the radioactive label incorporated and this is attributable solely to PARP activity.

Further details of the assay are given below.

Materials

The materials used included the following:
DTT (Dithiothreitol)

A 100 mM (15.4 mg/ml) solution (for use as an antioxidant) was made up, divided into 500 μl aliquots and stored at –20° C.

| Hypotonic buffer: | |
| --- | --- |
| 9 mM Hepes | (214 mg/100 ml) |
| 4.5% Dextran | (4.5 g/100 ml) |
| 4.5 mM MgCl$_2$ | (92 mg/100 ml) |

The above ingredients were dissolved in about 80 ml distilled water, pH was adjusted to 7.8 (NaOH/HCl), the solution was then made up to 100 ml with distilled water, and stored in a refrigerator. DTT was added to 5 mM just before use (50 μl/ml).

| Isotonic buffer: | |
| --- | --- |
| 40 mM Hepes | (1.9 g/200 ml) |
| 130 mM KCl | (1.94 g/200 ml) |
| 4% Dextran | (8 g/200 ml) |
| 2 mM EGTA | (152 mg/200 ml) |
| 2.3 mM MgCl$_2$ | (94 mg/200 ml) |
| 225 mM Sucrose | (15.39 g/200 ml) |

The above ingredients were dissolved in about 150 ml distilled water, pH was adjusted to 7.8 (NaOH/HCl), the solution was then made up to 200 ml with distilled water and stored in a refrigerator. DTT was added to 2.5 mM just before use (25 μl/ml).
NAD NAD was stored as a solid in pre-weighed aliquots at –20° C. From these, solutions of a concentration of approximately 6 mM (4–4.5 mg/ml) were freshly made up shortly before performing an assay, and the molarity was checked by measuring the optical density (O.D.) at 260 nm. The stock solution was then diluted with water to give a concentration of 600 μM and a small amount of 32P labelled NAD was added (e.g. 2–5 μl/ml).
Oligonucleotide The oligonucleotide having the palindromic sequence CGGAATTCCG, synthesised by conventional means, was vacuum dried and stored as pellets in a freezer. Before use, it was made up to 200 μg/ml in 10 mM Tris/HCl, pH 7.8, with each pellet being dissolved completely in 50 ml of buffer. The solution was then heated to 60° C. in a water bath for 15 minutes, and allowed to cool slowly to ensure correct reannealing. After adding 9.5 ml of buffer, the concentration was checked by measuring the optical density of a diluted sample at 260 nm. The main solution was then diluted to a concentration of 200 μg/ml and stored in 500 μl aliquots in a freezer, ready for use.

TCA

Solutions of TCA (Trichloroacetic acid) were prepared at two concentrations. 10% TCA+10% sodium pyrophosphate, and 1% TCA+1% sodium pyrophosphate.

Cells

The L1210 cells used as the source of the PARP enzyme were maintained as a suspension culture in RPMI medium+ 10% foetal bovine serum+glutamine and antibiotics (penicillin and streptomycin). HEPES and sodium bicarbonate were also added, and the cells were seeded in 100 ml of medium such that there would be a concentration of approximately $8 \times 10^5$/ml at the time of carrying out an assay.

Method

The compounds being tested were generally made up as a concentrated solution in DMSO (Dimethyl sulphoxide). The solubility of the compound was then checked by adding a quantity of the DMSO solution to a quantity of the isotonic buffer, in the required final proportions that were to be used in carrying out the assay, and after an interval the solution was examined under a microscope for any signs of crystals forming.

A desired quantity of the cells, ascertained by counting with a haemocytometer, was then centrifuged (1500 rpm in a "Europa" model 24M centrifuge for 5 minutes), the supernatant removed, and the pellets obtained were resuspended in 20 ml Dul A at 4° C. before centrifuging again at 1500 rpm and 4° C. After again removing the supernatant, the cells were resuspended at a concentration of $3 \times 10^7$ cells/ml in ice cold hypotonic buffer and left for 30 minutes on ice. Nine volumes were then added of ice cold isotonic buffer, and the cells, now rendered permeable to exogenous $NAD^+$, were then used within the next hour for carrying out an assay. The permeablisation of the cells may be checked at this stage by adding duplicate aliquots of cells to an equal volume of trypan blue, leaving for 5 minutes and then counting on a haemocytometer.

The assay was then carried out using for convenience plastic 15 ml conical bottomed assay tubes set up in a shaking water bath at 26° C. which is the optimum temperature for this enzyme. In a typical assay using the oligonucleotide solution at a concentration of 5 μg/ml and the test compound/DMSO solution at a concentration of 2%, and carrying out the assay in quadruplicate, there would then be placed in each assay tube 5 μl of the oligonucleotide solution, 50 μl of the 600 μm NAD+[$^{32}$P]-NAD solution, 8 μl of the test compound/DMSO solution, and 37 μl of water. Prior to the start of the experiment this "cocktail" would be pre-warmed for 7 minutes at 26° C., as would be also the cell suspension. The reaction would then be started by adding 300 μl of the cell suspension. The reaction would be stopped by adding 2 ml of the 10% TCA+10% sodium pyrophosphate solution.

In addition to the above, six assay tubes would usually be set up as blanks, these containing the same ingredients as above but, before adding the cell suspension, TCA solution is added to prevent any reaction from taking place. This enables corrections to be applied for any non-specific binding of the labelled material to the filter used (see below).

After adding the cell suspension at timed intervals to each of the assay tubes, the 10% TCA+10% sodium pyrophosphate at 4° C. was added to each assay tube exactly 5 minutes after addition of the cell suspension to that tube. Then, after leaving the tubes on ice for a minimum time of one hour, the contents of each individual tube were filtered through an individual filter funnel of a suction filter apparatus using GF/C filter elements (rough side up) wetted with 10% TCA. After filtering the contents of each tube and rinsing the filters several times with 1% TCA+1% sodium pyrophosphate solution, the filters were carefully removed and dried before being placed in individual scintillation vials. Four additional scintillation vials were also set up as reference standards containing 10 μl of the 600 μM NAD+ [$^{32}$P]-NAD solution, 10 ml scintillant then being added to each vial. Counting was carried out for 2 minutes on a β counter to obtain measures of the $^{32}$P present, and thus the amount of the poly(ADP-ribose) and activity of the PARP enzyme.

RESULTS OF IN VITRO PARP INHIBITION STUDIES

Apart from applying the PARP enzyme assay in accordance with the standard procedure outlined above to a range of compounds which have been made in accordance with the present invention, for comparison purposes it was also applied to certain benzamide compounds, in particular 3-hydroxybenzamide, 3-methoxybenzamide and 3-aminobenzamide, that are already known to exhibit certain PARP inhibitory activity. A full tabulated list of the compounds which have been made and/or studied is hereinafter presented in TABLE III, together with the PARP inhibition assay results obtained in different experiments for different concentrations of the compounds when tested using the assay hereinabove described.

In reviewing this list, the known PARP inhibitors 3-aminobenzamide, 3-methoxybenzamide and 3-hydroxybenzamide may be regarded as reference compounds. Although there is considerable variation in activity, and in some cases at least the higher concentrations for aqueous solutions of the test compounds could not be achieved because of low solubility, in general the compounds of the present invention which were tested showed a useful degree of activity. Of especial interest were the benzoxazole analogues, particularly those having the reference numbers NU1056, NU1040, NU1051 and NU1054, which showed relatively high inhibitory activity even at low concentrations. Also of especial interest as potent PARP inhibitors are the quinazolinone derivatives which have been mentioned, particularly compounds NU1025, NU1057, NU1063, NU1068 and NU1069.

In contrast to the results obtained for the compounds of the present invention, which have in many cases showed PARP enzyme inhibitory properties that are well above average and at least comparable with, if not considerably better than, those of other known benzamide PARP inhibitors, various analogous nicotinamide compounds studied showed no, or very poor, inhibitory activity when tested in the same manner at similar concentrations.

FURTHER BIOLOGICAL ACTIVITY STUDIES

Again using cultures of the murine leukaemia L1210 cell line, growth inhibition experiments were carried out to assess the cytostatic effects of the compounds and clonogenic survival assays were performed to assess cytotoxicity, especially in relation to use of the compounds in conjunction with DNA damaging cytotoxic agents such as cytotoxic antitumour drugs or high energy radiation. DNA damage and the effect of the PARP inhibitors on the process of DNA strand break formation and repair has also been assessed by carrying out DNA strand break assays and monitoring by alkaline elution in accordance with published techniques.

By way of example some further details are given below of studies carried out using the quinazolinine compounds identified by the reference numbers NU1025 and NU1057 (derivable by molecular rearrangement of corresponding benzoxazole compounds) as representative examples of the PARP inhbiting compounds of the present invention, and also using for comparison the known PARP inhibitors 3-aminobenzamide (3AB) and benzamide (BZ) itself. Results of experiments using the alkylating agent temozolomide (TM) are also reported, taking this as a illustrative example of a cytotoxic DNA damaging antitumour drug, and in some of the studies carried out gamma ray irradiation was used to damage the cells.

In the growth inhibition assays, typically the L1210 cells would be seeded at $1 \times 10^4$/ml in triplicate in 24 well multidishes, and 24 hours later the compounds or drugs being tested would be added in selected combinations and concentrations. At this time one set of replicates would be counted using a Coulter counter ($N_0$), and 48 hours later the remaining samples would be counted ($N_1$). The percentage (%) growth inhibition of drug-treated samples could then be estimated. In drug combination experiments, where evidence of synergistic effects on cell growth or clonogenicity was being sought, a single, fixed concentration of a cytotoxic drug sample, e.g. temozolomide, would be taken as the control value.

As an illustration of the results obtained, there is shown in TABLE I at the end of this description the $IC_{50}$ values of the above-mentioned PARP inhibitors when used alone-and in conjunction with a fixed concentration (100 $\mu$M) of temozolomide, as estimated from the growth inhibition experiments. Although not shown, it may be noted that exposure of the cells to TM alone caused inhibition of cell growth with an $IC_{50}$ value of 361±25 $\mu$M. Also, it was established that co-exposure of the cells to 100 $\mu$M TM with increasing concentrations of the PARP inhibitors caused a synergistic increase in growth inhibition throughout a range of concentrations.

It will be seen from Table I that 10–20 fold higher concentrations of the compound NU1025 used alone were required to inhibit cell growth than were required when the compound was used in conjunction with 100 $\mu$M TM. For example, the $IC_{50}$ of NU1025 alone was 0.41 mM, and this was reduced to 0.04 mM in the presence of TM. In comparison, only 2–3 fold differences were obtained with 3AB and BZ, where there was considerable overlap between the growth inhibitory effects of the compounds per se and their effects in conjunction with TM. An identical rank order was obtained when comparing the effectiveness of the compounds as PARP inhibitors and their ability to inhibit cell growth which at least suggests that PARP function is essential for cell growth.

In the clonogenic survival assays, typically the L1210 cells were exposed to varying concentrations of TM± a fixed concentration of PARP inhibitor for a fixed time of 16 hours, prior to counting and seeding for colony formation in 0.12–0.15% agarose in drug-free medium. After 7–10 days colonies were stained with 0.5 mg/ml MTT and counted by eye on a gridded light box. Survival curves were plotted and typical $DEF_{10}$ values obtained are hereinafter given in Table II ($DEF_{10}$ being defined as the ratio of the concentration of TM that reduces survival to 10% divided by the concentration of TM that reduces survival to 10% in the presence of a fixed concentration of PARP inhibitor). Each $DEF_{10}$ value in Table II represents the average ratio ± S.E. (standard error) derived from the averaged 10% survival for TM alone (675±31 $\mu$M from 22 independent survival curves) divided by individual 10% survival values from at least 3 independent survival curves performed in the presence of a fixed concentration of inhibitor.

A reasonable correlation was found between growth inhibitory effects and cytotoxic effects for TM alone with an $IC_{50}$ value of 361 $\mu$M±25 $\mu$M and a $LD_{50}$ value of 251±13 $\mu$M respectively, despite differing exposure times (48 hours for growth inhibition and 16 hours for cytotoxicity). TM has a half life in culture of about 40 minutes, and therefore will exert its full effects well before the minimum duration of exposure of either experiment. All compounds potentiated TM cytotoxicity, but NU1025 produced about the same $DEF_{10}$ values at very much lower concentrations than 3AB and BZ respectively. For example, 50 $\mu$M NU1025 and 5 mM 3AB gave equivalent $DEF_{10}$ values of about 4. For NU1025 maximal potentiation of cytotoxicity was obtained by a concentration in the range of 50–100 $\mu$M, and was significant at doses as low as 10 $\mu$M.

In other clonogenic survival assays gamma ray irradiation was used to damage the cells. Typically, L1210 cells (3 ml, $4 \times 10^3$/ml in plastic bijoux bottles) were irradiated at 40° C. with varying doses of gamma rays in the presence or absence of 10 mM 3AB or 200 $\mu$M NU1057 and a final concentration of 2% DMSO. The cells were then incubated at 37° C. for 2 hours in the continued presence or absence of PARP inhibitor prior to seeding for colony formation. A significant potentiation of gamma ray cytotoxicity by NU1057 was observed, with a $DEF_{10}$ of 1.1.

Repair of potentially lethal damage (PLD) occurs when cells are held in stationary-phase following initiation of PLD prior to allowing cell division to take place. In further typical experiments, L1210 cells were allowed to repair gamma ray PLD in the presence or absence of 3AB or NU1025 as follows. L1210 cells were maintained in culture until they had attained stationary phase (>$10^6$cells/ml). They were diluted to $1.5 \times 10^5$/ml in conditioned medium from stationary-phase cultures to prevent further cell division. Replicate 2 ml samples of cells in plastic bijoux were held on ice prior to and immediately following 8 Gray gamma ray irradiation. 1 ml of 3× final concentration of compounds 3AB or NU1025 made up in conditioned medium from stationary cultures was added (to give final concentrations of $10^6$cells/ml in 1% DMSO±10 mM 3AB or 200 $\mu$M NU1025) and the cells were incubated at 37° C. for 0, 2 or 4 hours prior to resuspending in drug-free medium and seeding for colony formation. Unirradiated stationary phase cultures incubated at 37° C. for 0, 2 or 4 hours with 1% DMSO±10 mM 3AB or 200 $\mu$M NU1025 were used as appropriate controls for determining relative cell survival. In the absence of PARP inhibitor cell survival increased with time allowed for PLD repair to take place. For example, when seeded immediately after irradiation (no repair) only about 0.2% of the cells survived, but after a 4 hour repair period this had increased to 0.7%. It was observed that both 3AB and NU1025 blocked this repair.

The cytotoxic effects of the PARP inhibiting compounds alone has also been investigated. In one set of experiments, the $LD_{50}$ values for a 24 hours exposure of L1210 cells were 14±1.0 mM (3AB); 6.0±1.5 mM (BZ) and 1.6±0.1 Mm (NU1025). The $LD_{50}$ values differed by $\leq$3-fold from the $IC_{50}$ values but maintained the same rank order with respect to their potency as PARP inhibitors. In agreement with the growth inhibition data there was $\geq$10-fold difference between the concentration of NU1025 needed to produce maximal potentiation of TM cytotoxicity and the concentration needed to produce cytotoxicity per se.

In respect of DNA strand break assays carried out, it was found that a 1 hour treatment with TM resulted in a concentration-dependent increase in the rate of elution which provides a measure of the extent of DNA strand breakage. Changes in DNA strand break levels were detectable at levels of TM as low as 150 μM, a concentration which reduced survival by about 30%. All the compounds were tested for their ability to produce strand breaks when used alone. A 24 hour incubation of cells with 1 mM NU1025, and 20 mM 3AB or BZ had no significant effect on DNA strand break levels compared to untreated cells. However, coincubation for 1 hour of a fixed concentration of TM (150 μM) with increasing concentrations of all PARP inhibitors tested caused a progressive increase in the rate of elution (extent of strand breakage) compared to TM alone.

The results for all the 3 representative compounds mentioned have been summarised by plotting values of a parameter related to extent of strand breakage versus inhibitor concentration. For all the compounds, the strand breakage increased linearly with increasing concentration, but values started increasing significantly for NU1025 at about 100 μM, whereas concentrations above 3 mM and 5 mM were required to significantly increase values for BZ and 3AB respectively. Again, the rank order and potency of the compounds in the DNA strand break assay demonstrated an excellent correlation with in vitro PARP inhibitory potency.

Overall, it is believed that the studies carried out give clear evidence that the PARP inhibitory characteristics of compounds of this invention reflects an ability of these compounds to potentiate the cytotoxicity of DNA damaging agents such as certain cytotoxic antitumour drugs and radiation used in radiotherapy. Accordingly, such compounds should be especially useful for administration in conjunction with such cytotoxic drugs or radiotherapy to potentiate their effect in the course of medical treatment as hereinbefore indicated.

Summary

Although the present invention should be regarded overall as comprising each and every novel feature or combination of features disclosed herein, the main aspects of the invention comprise, principally but not exclusively, broadly the following:

(i) Novel compounds of formula (I), (II) or (IV) as defined herein;

(ii) Compounds of formula (I), (II) or (IV) with substituents as hereinbefore defined (including salts thereof) for therapy or for use in medicine and in the manufacture of medical preparations, useful for example as PARP inhibitors to be administered in conjunction with cytotoxic drugs or with radiotherapy to potentiate the effectiveness of the latter in treatment of cancer;

(iii) Processes for the preparation of novel compounds of formula (I), (II) or (IV) as defined herein, including any novel intermediate compounds produced in carrying out such processes;

(iv) Pharmaceutical formulations comprising a compound of formula (I), (II) or (IV) as defined herein together with a pharmaceutically acceptable carrier therein;

(v) Processes for the preparation of a pharmaceutical formulation as defined in (iv) above, e.g. by methods referred to herein;

(vi) Quinazolinone compounds of formula (II), possibly representing molecularly rearranged compounds of formula (IV), as herein disclosed, for therapy or for use in medicine and in the manufacture of medical preparations, useful for example as PARP inhibitors to be administered in conjunction with cytotoxic drugs or with radiotherapy to potentiate the effectiveness of the latter in treatment of cancer, and pharmaceutical formulations comprising said quinazolinone compounds.

TABLE I

| INHIBITOR | $IC_{50}$ (mM) ± SE INHIBITOR ALONE | $IC_{50}$ (mM) ± SE INHIBITOR + 100 μM TM |
|---|---|---|
| 3-AMINOBENZAMIDE | 6.7 ± 0.2 | 2.5 ± 0.1 |
| BENZAMIDE | 2.5 ± 0.3 | 0.84 ± 0.12 |
| NU1025 | 0.41 ± 0.06 | 0.04 ± 0.003 |

TABLE II

| INHIBITOR | CONCENTRATION | $DEF_{10}$ |
|---|---|---|
| 3-AMINOBENZAMIDE | 1 mM | 2.4 ± 0.3 |
| | 5 mM | 4.1 ± 0.4 |
| BENZAMIDE | 1 mM | 4.0 ± 0.7 |
| | 3 mM | 6.9 ± 0.2 |
| NU1025 | 10 μM | 2.0 ± 0.2 |
| | 50 μM | 4.0 ± 0.5 |
| | 100 μM | 5.1 ± 0.7 |

TABLE III

| House Number | Name | Structure | % Inhibition 10 μM | 30 μM | 100 μM |
|---|---|---|---|---|---|
| Ref | 3-hydroxybenzamide $C_7H_7NO_2$ MW = 137 | 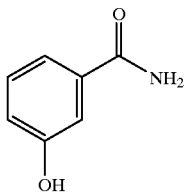 | 35 | 59 | 81 |

TABLE III-continued

| House Number | Name | Structure | % Inhibition | | |
|---|---|---|---|---|---|
| | | | 10 μM | 30 μM | 100 μM |
| Ref | 3-methoxybenzamide<br>$C_8H_9NO_2$<br>MW = 151 | | 55 | 78 | 89 |
| Ref | 3-aminobenzamide<br>$C_7H_8N_2O_2$<br>MW = 136 | | 36 | 63 | 79 |
| NU1005 | 3-benzyloxybenzamide<br>$C_{14}H_{13}NO_2$<br>MW = 227 | 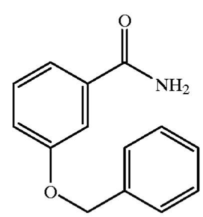 | 34 | 60<br>59 | 76 |
| NU1006 | 3-(4-methoxybenzyloxy)<br>benzamide<br>$C_{15}H_{15}NO_3$<br>MW = 257 | 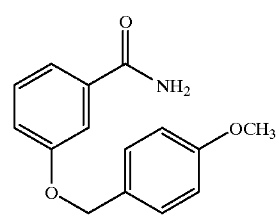 | 58 | 74 | insol. |
| NU1007 | 3-(4-nitrobenzyloxy)<br>benzamide<br>$C_{14}H_{12}N_2O_4$<br>MW = 272 | 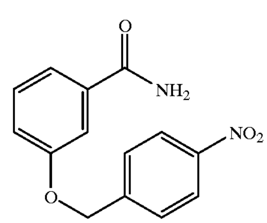 | 26 | insol. | insol. |
| NU1008 | 3-(cyclohexylmethyloxy)<br>benzamide<br>$C_{14}H_{19}NO_2$<br>MW = 233 | 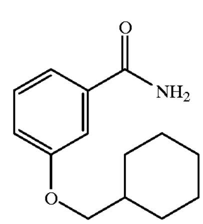 | insol. | insol. | insol. |

TABLE III-continued

| House Number | Name | Structure | % Inhibition | | |
|---|---|---|---|---|---|
| | | | 10 μM | 30 μM | 100 μM |
| NU1013 | 3-(4-azidobenzyloxy) benzamide $C_{14}H_{12}N_4O_2$ MW = 268 | 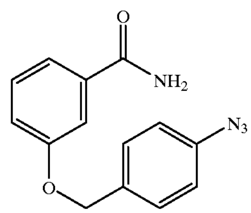 | 49 | 28 | 43 |
| NU1014 | 3-(4-bromobenzyloxy) benzamide $C_{14}H_{12}BrNO_2$ MW = 306 | 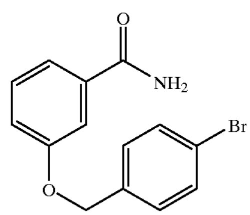 | 23 | 36 | insol. |
| NU1015 | 3-(4-fluorobenzyloxy) benzamide $C_{14}H_{12}FNO_2$ MW = 245 | 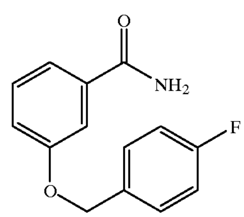 | 20 | 52 51 | insol. |
| NU1016 | 3-(4-aminobenzyloxy) benzamide $C_{14}H_{14}N_2O_2$ MW = 242 | 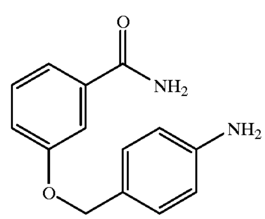 | 40 | 66 | 84 |
| NU1017 | 3-(3-nitrobenzyloxy) benzamide $C_{14}H_{12}N_2O_4$ MW = 272 | 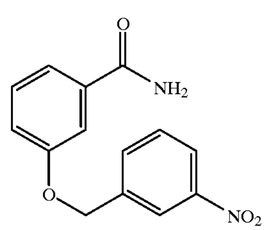 | 21 | 40 | insol. insol. |
| NU1019 | 3-(5-bromopentyloxy) benzamide $C_{12}H_{16}BrNO_2$ MW = 268 | 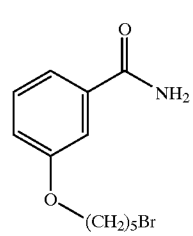 | | 54 | 81 |

TABLE III-continued

| House Number | Name | Structure | % Inhibition | | |
|---|---|---|---|---|---|
| | | | 10 μM | 30 μM | 100 μM |
| NU1020 | 3-(piperonyloxy) benzamide<br>$C_{15}H_{13}NO_4$<br>MW = 271 | 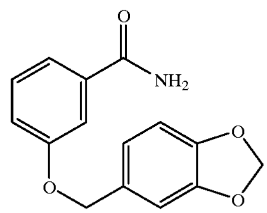 | 51 | 70 | 93 |
| NU1022 | 3-(8-adenos-9-yloctyloxy) benzamide<br>$C_{20}H_{26}N_6O_2$<br>MW = 382 | 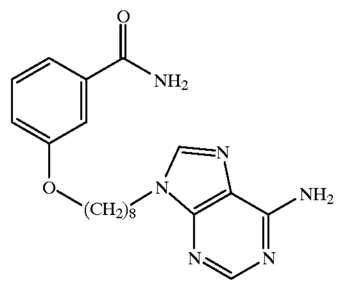 | 30 | | |
| NU1023 | 3-[5-(6-chloropurin-9-yl) pentyloxy]benzamide<br>$C_{17}H_{18}ClN_5O_2$<br>MW 360 | 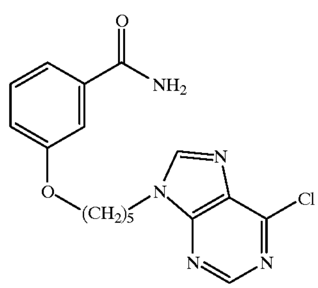 | 26 | 45 | 71 |
| NU1024 | 3-(5-adenos-9-ylpentyloxy)benzamide<br>$C_{17}H_{20}N_6O_2$<br>MW = 340 | 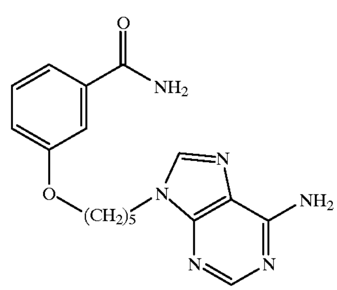 | 16 | 42 | 67 |
| NU1025 | 8-hydroxy-2-methyl quinazolin-4-[3H]one<br>$C_9H_8N_2O_2$<br>MW = 176 | 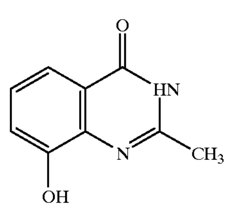 | 92<br>1 μM = 63<br>0.1 μM = 18<br>0.5 μM = 59<br>1.0 μM = 68<br>$IC_{50}$ = 0.4 μM | 92 | 96 |

TABLE III-continued

| House Number | Name | Structure | % Inhibition 10 μM | 30 μM | 100 μM |
|---|---|---|---|---|---|
| NU1026 | 8-hydroxyquinazolin-4-[3H]one<br>$C_8H_6N_2O_2$<br>MW = 162 | 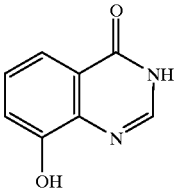 | 78<br>0.5 μM = 18<br>1.0 μM = 38<br>2.0 μM = 54<br>$IC_{50}$ = 2 μM | 87 | 95 |
| NU1027 | 3-[8-(6-chloropurin-9-yl)octyloxy]benzamide<br>$C_{20}H_{24}ClN_5O_2$<br>MW = 402 | 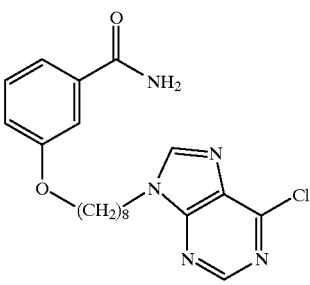 | 30 | insol. | insol. |
| NU1029 | 3-(12-adenos-9-yldodecyloxy)benzamide<br>$C_{24}H_{34}N_6O_2$<br>MW = 438 | 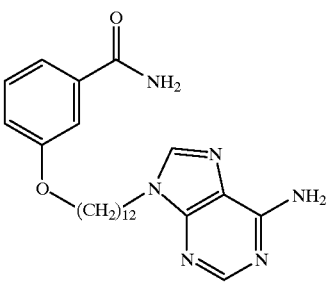 | 26 | 51 | 74 |
| NU1030 | 3-(N-acetyl-4-amino benzyloxy)benzamide<br>$C_{16}H_{16}N_2O_3$<br>MW = 284 | 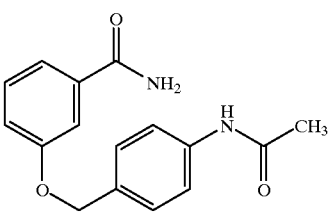 | 49 | 70 | 34 |
| NU1031 | 3-allyloxybenzamide<br>$C_{10}H_{11}NO_2$<br>MW = 177 | 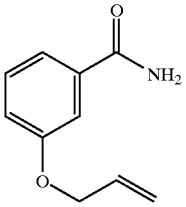 | 21 | 58 | 80 |
| NU1034 | 2,5-methylenedioxy benzamide<br>$C_8H_7NO_3$<br>MW = 165 | 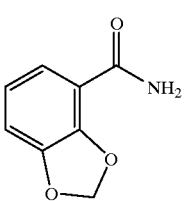 | 66<br>$IC_{50}$ = 5.3 μM | | 94 |

TABLE III-continued

| House Number | Name | Structure | % Inhibition | | |
|---|---|---|---|---|---|
| | | | 10 μM | 30 μM | 100 μM |
| NU1036 | 3-(4-trifluoromethyl benzyloxy)benzamide<br>$C_{15}H_{12}F_3NO_2$<br>MW = 295 | 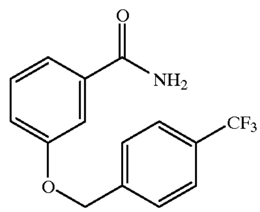 | 3 | 13 | 10 |
| NU1037 | 3-(4-cyanobenzyloxy) benzamide<br>$C_{15}H_{12}N_2O_2$<br>MW = 252 | 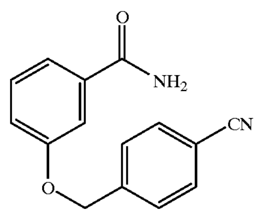 | 33 | insol. | insol. |
| NU1038 | 3-butoxybenzamide<br>$C_{11}H_{15}NO_2$<br>MW = 193 | 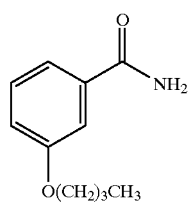 | 23 | 50 | 78 |
| NU1039 | 3-pentyloxybenzamide<br>$C_{12}H_{17}NO_2$<br>MW = 207 | 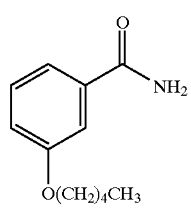 | 18 | 45 | 66 |
| NU1040 | 2-t-butylbenzoxazole-4-carboxamide<br>$C_{12}H_{14}N_2O_2$<br>MW = 218 | 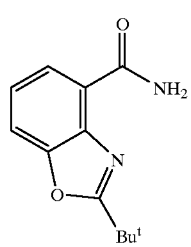 | 87<br>$IC_{50}$ = 8.4 μM | 88 | 93 |
| NU1041 | 3-(4-carboxymethyl benzyloxy)benzamide<br>$C_{16}H_{15}NO_4$<br>MW = 285 | 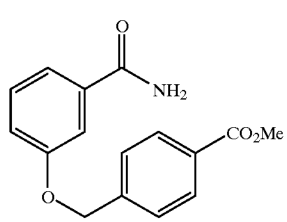 | insol. | insol. | insol. |

TABLE III-continued

| House Number | Name | Structure | % Inhibition | | |
|---|---|---|---|---|---|
| | | | 10 μM | 30 μM | 100 μM |
| NU1042 | 3-(2-nitrobenzyloxy) benzamide<br>$C_{14}H_{12}N_2O_4$<br>MW = 272 | 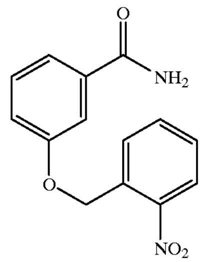 | insol. | insol. | insol. |
| NU1043 | 3-hexyloxybenzamide<br>$C_{13}H_{19}NO_2$<br>MW = 221 | 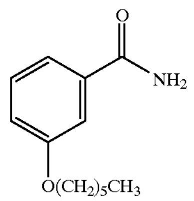 | 15 | 39 | insol. |
| NU1044 | 3-heptyloxybenzamide<br>$C_{14}H_{21}NO_2$<br>MW = 235 | 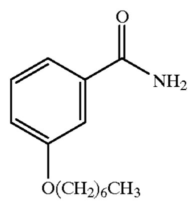 | 26 | insol. | insol. |
| NU1045 | 3-octyloxybenzamide<br>$C_{15}H_{23}NO_2$<br>MW = 249 | 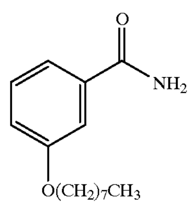 | insol. | insol. | insol. |
| NU1048 | 3-phenethyloxybenzamide<br>$C_{15}H_{15}NO_2$<br>MW = 241 | 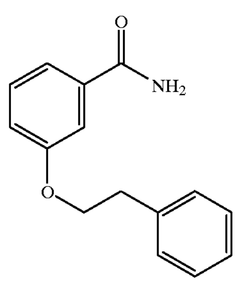 | 30 | 50 | 72 |
| NU1050 | 3-cinnamyloxybenzamide<br>$C_{16}H_{15}NO_2$<br>MW = 253 | 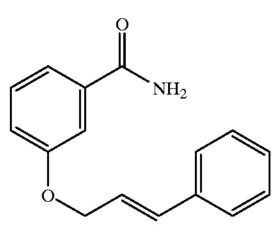 | 23 | insol. | insol. |

TABLE III-continued

| House Number | Name | Structure | % Inhibition | | |
|---|---|---|---|---|---|
| | | | 10 μM | 30 μM | 100 μM |
| NU1051 | 2-phenylbenzoxazole-4-carboxamide<br>$C_{14}H_{10}N_2O_2$<br>MW = 238 | | 82<br>$IC_{50}$ = 2.1 μM | | |
| NU1052 | 3-(4-carboxybenzyloxy) benzamide<br>$C_{15}H_{13}NO_4$<br>MW = 271 | | | | |
| NU1054 | 2(4-methoxyphenyl) benzoxazole-4-carboxamide<br>$C_{15}H_{12}N_2O_2$<br>MW = 252 | | $IC_{50}$ = 1.1 μM | | |
| NU1056 | 2-methylbenzoxazole-4-carboxamide<br>$C_9H_8N_2O_2$<br>MW = 176 | | $IC_{50}$ = 9.5 μM | | |
| NU1057 | 8-hydroxy-2-(4-nitrophenyl)-quinazolin-4-one<br>$C_{14}H_9N_3O_4$<br>MW = 283.2 | | 92<br>$IC_{50}$ = 0.23 μM | | |

TABLE III-continued

| House Number | Name | Structure | % Inhibition 10 μM | 30 μM | 100 μM |
|---|---|---|---|---|---|
| NU1063 | 8-methoxy-2-methylquinazolin-4[3H]-one $C_{10}H_{10}N_2O_2$ MW = 190.2 | 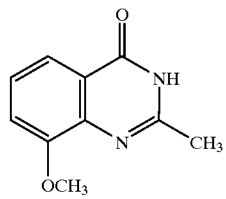 | $IC_{50} = 0.78\ \mu M$ | | |
| NU1065 | 8-methoxy-2-phenylquinazolin-4[3H]-one $C_{15}H_{12}N_2O_2$ MW = 252.27 | 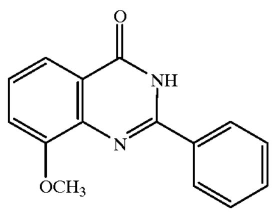 | $IC_{50} = 4.2\ \mu M$ | | |
| NU1068 | 8-hydroxy-2-phenylquinazolin-4[3H]-one $C_{14}H_{10}N_2O_2$ 238.24 | 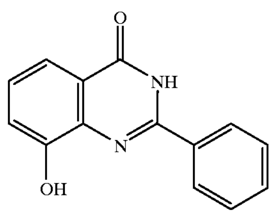 | $IC_{50} = 0.53\ \mu M$ | | |
| NU1069 | 2,8-dimethylquinazolin-4[3H]-one $C_{10}H_{10}N_2O_2$ 174.2 | 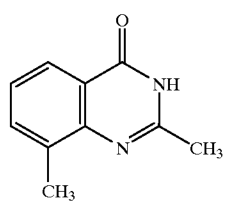 | $IC_{50} = 0.2\ \mu M$ | | |

We claim:

1. A compound of formula I

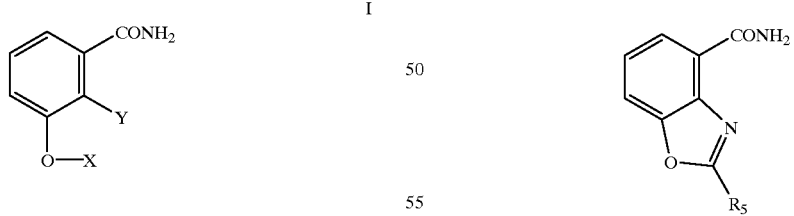

or a pharmaceutically acceptable salt thereof, wherein Y and X together form a bridge —Y—X— which represents the grouping

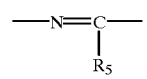

where $R_5$ is H, alkyl, optionally substituted aryl or optionally substituted aralkyl.

2. A compound according to claim 1 wherein $R_5$ is alkyl of 1–6 carbons.

3. A benzoxazole carboxamide according to claim 1 which has the structural formula IV

IV

4. A benzoxazole carboxamide according to claim 3 wherein $R_5$ is alkyl, phenyl, naphthyl, benzyl or pyridyl.

5. A compound as claimed in claim 3 wherein $R_5$ is an alkyl of 1–6 carbons.

6. A compound as claimed in claim 3 selected from the group consisting of:

(a) 2-methylbenzoxazole-4-carboxamide;

(b) 2-t-butylbenzoxazole-4-carboxamide;

(c) 2-phenylbenzoxazole-4-carboxamide;

(d) 2-(4-methoxyphenyl)benzoxazole-4-carboxamide; or a pharmaceutically acceptable salt thereof.

7. A pharmaceutical composition in unit dosage form for use in inhibiting poly(ADP-ribose) polymerase activity comprising an effective amount of a compound according to claim 1, and a pharmaceutically acceptable carrier.

8. A method for inhibiting PARP activity in a mammal in need of such inhibition, said method comprising administering to said mammal, an effective amount of a compound according to claim 1.

9. A method of improving cytotoxic effectiveness of cytotoxic drugs or radiotherapy which comprises administering to a mammal in need of such treatment an effective amount of a compound according to any one of claims 1 to 6.

* * * * *